(12) United States Patent
Sack et al.

(10) Patent No.: US 8,518,117 B2
(45) Date of Patent: Aug. 27, 2013

(54) DISC FUSION IMPLANT

(75) Inventors: James A. Sack, Elverson, PA (US);
Mohit K Bhatnagar, Potomac, MD (US); Jack Y Yeh, North Potomac, MD (US)

(73) Assignee: JMEA Corporation, Rockville, MD (US)

( * ) Notice: Subject to any disclaimer, the term of this patent is extended or adjusted under 35 U.S.C. 154(b) by 756 days.

(21) Appl. No.: 12/038,613

(22) Filed: Feb. 27, 2008

(65) Prior Publication Data
US 2009/0012621 A1    Jan. 8, 2009

Related U.S. Application Data

(63) Continuation of application No. 11/774,584, filed on Jul. 7, 2007, now Pat. No. 7,922,767.

(51) Int. Cl.
*A61F 2/44*    (2006.01)

(52) U.S. Cl.
USPC .................. 623/17.16; 623/17.11; 623/17.13

(58) Field of Classification Search
USPC ........................................... 623/17.11–17.16
See application file for complete search history.

(56) References Cited

U.S. PATENT DOCUMENTS

| | | | |
|---|---|---|---|
| 3,741,205 A | 6/1973 | Markolf et al. | |
| 4,834,757 A | 5/1989 | Brantigan | |
| 5,171,280 A | * | 12/1992 | Baumgartner ............ 623/17.12 |
| 5,190,545 A | 3/1993 | Corsi et al. | |
| 5,405,391 A | 4/1995 | Hednerson et al. | |
| 5,423,826 A | 6/1995 | Coates et al. | |
| 5,439,464 A | 8/1995 | Shapiro | |
| 5,545,165 A | 8/1996 | Biedermann et al. | |
| 5,676,667 A | 10/1997 | Hausman | |
| 5,676,702 A | 10/1997 | Ratron | |
| 5,902,231 A | 5/1999 | Foley et al. | |
| 5,919,235 A | 7/1999 | Husson et al. | |
| 5,976,146 A | 11/1999 | Ogawa et al. | |
| 6,264,656 B1 | 7/2001 | Michelson | |
| 6,273,889 B1 | 8/2001 | Richelsoph | |
| 6,371,968 B1 | 4/2002 | Kogasaka et al. | |
| 6,432,106 B1 | 8/2002 | Fraser | |
| 6,436,103 B1 | 8/2002 | Suddaby | |

(Continued)

FOREIGN PATENT DOCUMENTS

FR    2712486    5/1995

OTHER PUBLICATIONS

U.S. Appl. No. 11/740,181, filed Apr. 25, 2007, and entitled "Prosthesis with a Selectively Applied Bone Growth Promoting Agent."

(Continued)

*Primary Examiner* — Michael T Schaper
(74) *Attorney, Agent, or Firm* — Plumsea Law Group, LLC

(57) ABSTRACT

An embodiment provides an implant prosthesis. In some cases, the prosthesis can take the form of an implant strip that may be implanted through the use of a surgical procedure that minimizes incision sizes and may be considered less invasive than typical spinal implant procedures. In one aspect, a spinal prosthesis may include an implant strip configured for insertion between two adjacent vertebrae, the implant strip including a first portion having a first rigidity and a second portion having a second rigidity that is less than the first rigidity, wherein the second portion is configured to deflect under an axial load before the first portion deflects.

20 Claims, 20 Drawing Sheets

(56) References Cited

U.S. PATENT DOCUMENTS

| | | |
|---|---|---|
| 6,447,512 B1 | 9/2002 | Landry et al. |
| 6,488,710 B2 | 12/2002 | Besselink |
| 6,524,312 B2 | 2/2003 | Landry et al. |
| 6,530,926 B1 | 3/2003 | Davison |
| 6,533,790 B1 | 3/2003 | Liu |
| 6,565,571 B1 | 5/2003 | Jackowski et al. |
| 6,610,094 B2 * | 8/2003 | Husson ............... 623/17.16 |
| 6,616,671 B2 | 9/2003 | Landry et al. |
| 6,620,196 B1 * | 9/2003 | Trieu ................... 623/17.16 |
| 6,656,178 B1 | 12/2003 | Veldhuizen et al. |
| 6,660,037 B1 | 12/2003 | Husson et al. |
| 6,800,084 B2 | 10/2004 | Davison et al. |
| 6,811,558 B2 | 11/2004 | Davison et al. |
| 7,901,460 B2 | 3/2011 | Sherman |
| 7,922,767 B2 | 4/2011 | Sack et al. |
| 2002/0107573 A1 | 8/2002 | Steinberg |
| 2002/0198533 A1 | 12/2002 | Geisler et al. |
| 2003/0073998 A1 | 4/2003 | Pagliuca et al. |
| 2003/0135216 A1 | 7/2003 | Sevrain |
| 2003/0171753 A1 | 9/2003 | Collins et al. |
| 2003/0175075 A1 | 9/2003 | Garrison |
| 2003/0225409 A1 | 12/2003 | Freid et al. |
| 2004/0034351 A1 | 2/2004 | Sherman et al. |
| 2004/0082960 A1 | 4/2004 | Davison |
| 2004/0106924 A1 | 6/2004 | Ralph et al. |
| 2004/0116931 A1 | 6/2004 | Carlson |
| 2004/0127902 A1 | 7/2004 | Suzuki et al. |
| 2004/0176842 A1 | 9/2004 | Middleton |
| 2004/0186482 A1 | 9/2004 | Kolb et al. |
| 2004/0204716 A1 | 10/2004 | Fanger et al. |
| 2004/0204717 A1 | 10/2004 | Fanger et al. |
| 2004/0215199 A1 | 10/2004 | Zinkel |
| 2004/0215341 A1 | 10/2004 | Sybert et al. |
| 2004/0230309 A1 * | 11/2004 | DiMauro et al. ........... 623/17.12 |
| 2004/0253185 A1 | 12/2004 | Herweck et al. |
| 2005/0004573 A1 | 1/2005 | Abdou |
| 2005/0015088 A1 | 1/2005 | Ringeisen |
| 2005/0090822 A1 | 4/2005 | DiPoto |
| 2005/0119750 A1 | 6/2005 | Studer |
| 2006/0041313 A1 | 2/2006 | Allard et al. |
| 2006/0111715 A1 | 5/2006 | Jackson |
| 2006/0142858 A1 | 6/2006 | Colleran et al. |
| 2006/0149279 A1 | 7/2006 | Mathews |
| 2006/0229615 A1 | 10/2006 | Abdou |
| 2006/0264948 A1 | 11/2006 | Williams |
| 2007/0010826 A1 | 1/2007 | Rhoda et al. |
| 2007/0093906 A1 | 4/2007 | Hudgins et al. |
| 2007/0123986 A1 * | 5/2007 | Schaller ............... 623/17.11 |
| 2007/0150064 A1 | 6/2007 | Ruberte et al. |
| 2007/0233071 A1 | 10/2007 | Dewey et al. |
| 2007/0270812 A1 | 11/2007 | Peckham |
| 2007/0270858 A1 | 11/2007 | Trieu et al. |
| 2008/0133012 A1 | 6/2008 | McGuckin |
| 2008/0255664 A1 | 10/2008 | Hogendijk et al. |
| 2009/0012622 A1 | 1/2009 | James et al. |
| 2009/0082810 A1 | 3/2009 | Bhatnagar et al. |
| 2012/0221107 A1 | 8/2012 | Sack et al. |

OTHER PUBLICATIONS

U.S. Appl. No. 11/840,707, filed Aug. 17, 2007, and entitled "Spinal Fusion Implants With Selectively Applied Bone Growth Promoting Agent."
International Seach Report and Written Opinion, mailed Aug. 12, 2009, from PCT Application No. PCT/US2008/069141.
Final Office Action, mailed May 7, 2010, in U.S. Appl. No. 11/859,386.
Office Action, mailed Aug. 10, 2009, in U.S. Appl. No. 11/859,386.
Office Action mailed Jun. 8, 2010 in U.S. Appl. No. 11/774,584.
Response to Office Action filed Jul. 8, 2010 in U.S. Appl. No. 11/774,584.
Office Action mailed Aug. 19, 2009 in U.S. Appl. No. 11/774,584.
Response to Office Action filed Dec. 17, 2009 in U.S. Appl. No. 11/774,584.
Interview Summary mailed Dec. 29, 2009 in U.S. Appl. No. 11/774,584.
Final Office Action mailed Apr. 1, 2010 in U.S. Appl. No. 11/774,584.
Office Action mailed Jun. 8, 2009 in U.S. Appl. No. 12/038,629.
Response to Office Action filed Jul. 8, 2009 in U.S. Appl. No. 12/038,629.
Office Action mailed Sep. 17, 2009 in U.S. Appl. No. 12/038,629.
Response to Office Action filed Dec. 17, 2009 in U.S. Appl. No. 12/038,629.
Interview Summary mailed Dec. 23, 2009 in U.S. Appl. No. 12/038,629.
Final Office Action mailed Apr. 1, 2010 in U.S. Appl. No. 12/038,629.
Request for Continued Examination filed Jul. 19, 2010 in U.S. Appl. No. 12/038,629.
Amendment accompanying Request for Continued Examination filed Jul. 19, 2010 in U.S. Appl. No. 12/038,629.
Office Action mailed Sep. 26, 2011 in U.S. Appl. No. 12/118,503.
Response to Office Action filed Jan. 25, 2012 in U.S. Appl. No. 12/118,503.
Notice of Allowance mailed Mar. 9, 2012 in U.S. Appl. No. 12/118,503.
Supplementary European Search Report mailed Mar. 7, 2012 in European Patent Application No. 08 781 335.8.
Office Action mailed Nov. 26, 2012 in U.S. Appl. No. 12/038,629.
Response to Supplementary European Search Report filed Oct. 5, 2012 in European Patent Application No. 08 781 335.8.

* cited by examiner

DISC FUSION IMPLANT

CROSS-REFERENCE TO RELATED APPLICATION

This application is a continuation of U.S. application Ser. No. 11/774,584, filed on Jul. 7, 2007, and entitled "Disk Fusion Implant", the entirety of which is incorporated herein by reference.

BACKGROUND OF THE INVENTION

1. Field of the Invention

The present invention relates generally to implantable prostheses and in particular to a spinal implant strip including a selectively applied bone growth promoting agent.

2. Description of Related Art

Spinal fusion implants have been previously proposed. In some cases, spinal fusion implants are embedded between adjacent vertebrae, partially or fully replacing the tissue disposed between the vertebrae.

One type of spinal fusion implant is the threaded spinal implant (commonly referred to as a spinal cage). This type of prosthesis is disclosed in Michelson (U.S. Pat. No. 6,264,656), the entirety of which is incorporated by reference. The threaded spinal implant is inserted between two adjacent vertebrae and is incorporated into the fusion of the bone along this portion of the spine.

Brantigan (U.S. Pat. No. 4,834,757) discloses plugs, used as spinal fusion implants, the entirety of which is incorporated by reference. The plugs are rectangular with tapered front ends and tool receiving rear ends. Generally, the plugs may be used in a similar manner to the spinal cages of Michelson. As with the spinal cages, the plugs may be inserted between adjacent vertebrae. The plugs may include nubs that behave like teeth, countering any tendency for the plugs to slip between the vertebrae. Generally, the spinal fusion implants disclosed require invasive surgery for implantation. Furthermore, these spinal fusion implants rigidly fix two adjacent bones together and do not allow for any motion. There is a need in the art for a type of spinal fusion implant that may be implanted through a minimally invasive procedure. There is also a need for fusion implants that can potentially accommodate motion.

SUMMARY OF THE INVENTION

A disc fusion implant is disclosed. In one aspect, the invention provides a spinal prosthesis, comprising: an implant strip including a first shape and a second shape and wherein the first shape is different than the second shape; the first shape being configured for installation through a tube; and where the second shape is coiled.

In another aspect, the second shape is a coil.

In another aspect, the first shape is a strip.

In another aspect, the implant strip is made of a material including titanium.

In another aspect, the strip is a shape memory material.

In another aspect, the shape memory alloy is made of a material selected from the group consisting essentially of: nickel, titanium, cobalt chrome, stainless steel, polymers, biological matrices and ceramics.

In another aspect, the invention provides a spinal prosthesis, comprising: an implant strip configured for insertion between two adjacent vertebrae; and where the implant strip is a shape memory alloy.

In another aspect, the implant strip is a corrugated strip.

In another aspect, a plurality of strips are used.

In another aspect, three or more implant strips are used.

In another aspect, the invention provides a method of implanting a spinal prosthesis, comprising the steps of: making an incision in a patients back; inserting a tube into the incision; inserting the spinal prosthesis through the tube; and implanting the spinal prosthesis between two adjacent vertebrae.

In another aspect, the spinal prosthesis is an implant strip.

In another aspect, the tube includes a curved tip that is configured to facilitate coiling of the implant strip.

In another aspect, the implant strip has a first shape and a second shape.

In another aspect, the implant strip has the first shape when the implant strip is inserted through the tube.

In another aspect, the implant strip has the second shape after the insertion of the implant strip is completed.

In another aspect, the first shape is a flat strip.

In another aspect, the second shape is a coil.

In another aspect, the invention provides a spinal prosthesis, comprising: an implant strip configured for implantation between two adjacent vertebrae; a bone growth promoting agent; and where the bone growth promoting agent is applied to the implant strip.

In another aspect, the implant strip includes a first portion.

In another aspect, the bone growth promoting agent is applied along the first portion.

In another aspect, the bone growth promoting agent is applied to the entirety of the implant strip.

In another aspect, the bone growth promoting agent is selectively applied to the implant strip.

In another aspect, the bone growth promoting agent is applied to a top surface of the implant strip and a bottom surface of the implant strip.

In another aspect, the invention provides a spinal prosthesis, comprising: an implant strip configured for insertion between two adjacent vertebrae; the implant strip comprising a first portion having a first rigidity and a second portion having a second rigidity that is less than the first rigidity; and where the second portion is configured to deflect under an axial load.

In another aspect, the first portion is made of a substantially non-deforming material.

In another aspect, the second portion is made of a substantially flexible material.

In another aspect, the second portion has a modified structure configured to decrease the rigidity of the second portion.

In another aspect, the second portion includes a deflecting portion.

In another aspect, the deflecting portion has an elliptic shape.

In another aspect, the second portion includes a motion limiting tab.

In another aspect, the second portion includes a cross bar configured to deflect and limit the axial motion and lateral movement of the implant strip.

In another aspect, the second portion is a protruding portion.

In another aspect, the protruding portion includes a plurality of slots.

In another aspect, the second portion is configured to partially permanently deflect.

In another aspect, the invention provides a spinal prosthesis configured for insertion between two adjacent vertebrae, a first vertebrae and a second vertebrae, comprising: an implant strip including a lateral dimension extending from a first lateral side portion to a second lateral portion, and wherein the implant strip includes a longitudinal dimension extending down the length of the implant strip; wherein the first lateral side of the implant strip is configured to engage the first vertebrae and wherein the second lateral side of the implant strip is configured to engage the second vertebrae; and wherein a first longitudinal portion of the implant strip forms a first inner coil, and wherein a second longitudinal portion of the implant strip forms a second outer coil, wherein the second outer coil is spaced radially outward of the first inner coil.

In another aspect, the first inner coil and the second inner coil are spaced to prevent contact with one another.

In another aspect, the first lateral side portion and the second lateral side portion comprise a first portion, and wherein a second portion is disposed between the first lateral side portion and the second lateral side portion; and wherein the second portion is less rigid than the first portion.

In another aspect, the second portion permits motion between the first lateral side portion and the second lateral side portion.

In another aspect, the first inner coil and the second inner coil are spaced to prevent contact with one another during motion.

In another aspect, the spinal prosthesis provides for continuity of a spine by providing a mechanical bridge between the first vertebrae and the second vertebrae.

In another aspect, the spinal prosthesis also allows motion between the first vertebrae and the second vertebrae.

In another aspect, an elastomeric material is disposed between the first lateral side portion and the second lateral portion, and wherein the first lateral side portion includes at least one protrusion engaging the elastomeric material.

In another aspect, the second lateral portion includes at least one protrusion engaging the elastomeric material.

Other systems, methods, features and advantages of the invention will be, or will become, apparent to one of ordinary skill in the art upon examination of the following figures and detailed description. It is intended that all such additional systems, methods, features and advantages be included within this description and this summary, be within the scope of the invention, and be protected by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like reference numerals designate corresponding parts throughout the different views.

FIG. 5-1 is a cross sectional view of a preferred embodiment of an implant strip with a bone growth promoting agent applied to the surface;

FIG. 5-2 is a cross sectional view of a preferred embodiment of an implant strip with a bone growth promoting agent that is selectively applied to the surface;

DETAILED DESCRIPTION OF THE PREFERRED EMBODIMENTS

Figure 1:
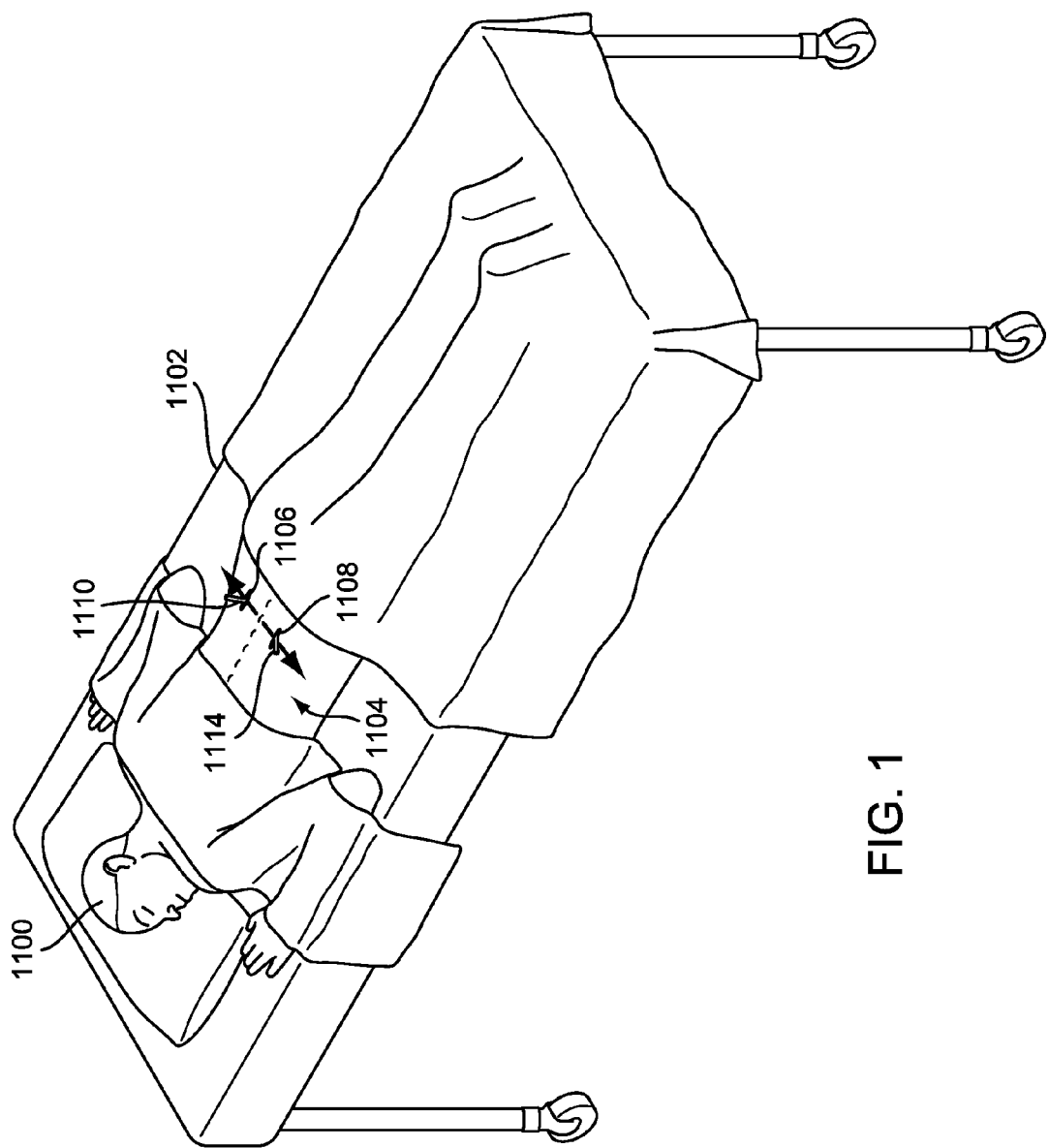
FIG. 1 is an isometric view of a preferred embodiment of a patient undergoing surgery.

FIG. 1 is an isometric view of a preferred embodiment of patient 1100 on operating table 1102. In this embodiment, patient 1100 is experiencing a surgical procedure to insert a spinal prosthesis. In particular, back 1104 of patient 1100 preferably includes first incision 1106 and second incision 1108. In a preferred embodiment, first incision 1106 includes first tube 1110 and second incision 1108 includes second tube 1114. Preferably, first incision 1106 and second incision 1108 are both less than one inch long. It should be understood that the placement of incisions 1106 and 1108 may be moved further together or closer apart and the location of incisions 1106 and 1108 in the current embodiment is only meant to be exemplary.

Figure 2:
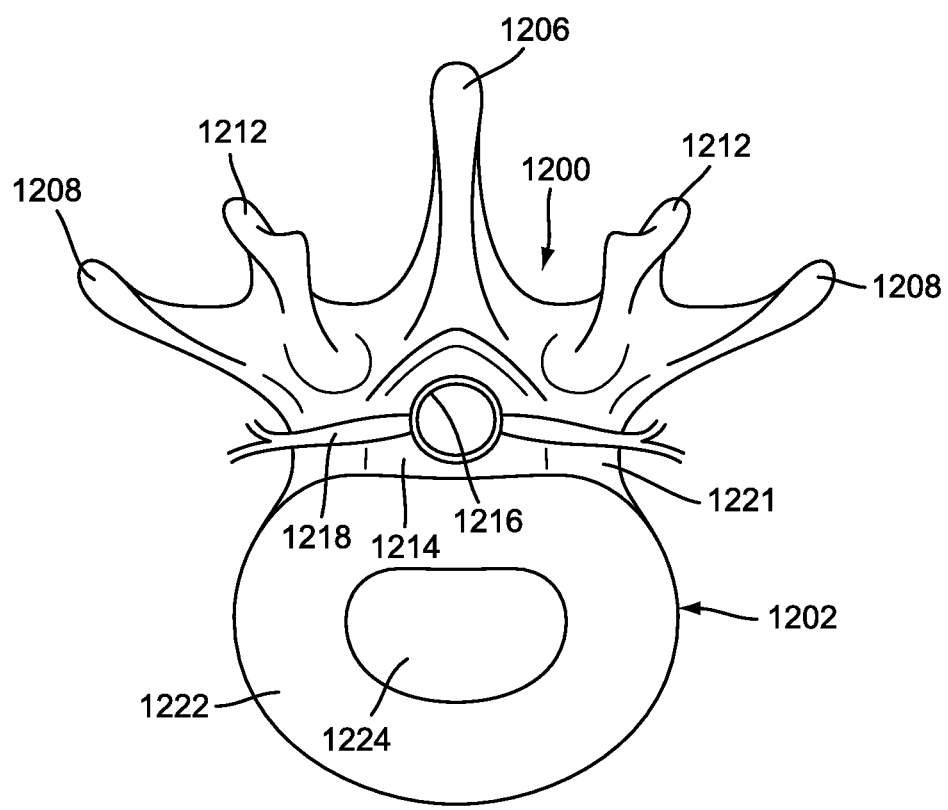
FIG. 2 is a plan view of a preferred embodiment of an intervertebral disc.

Preferably, first tube 1110 and second tube 1114 may be inserted into an intervertebral disc disposed between two adjacent vertebrae. FIG. 2 is a plan view of a single vertebra, shown generally at 1200, and an associated intervertebral disc 1202. (The anatomy shown in FIG. 2 is generally that of a lumbar vertebra, although the anatomy of thoracic, lumbar and cervical vertebra is similar; therefore, FIG. 2 can be considered to illustrate the basic principles of thoracic, lumbar and cervical vertebral anatomy.) The spinous process 1206 of the vertebra 1200 extends dorsally and can typically be palpated and felt through the skin of the back. Also in the dorsally-extending portion of the vertebra 1200 are two transverse processes 1208 and two mammillary processes and facet joints 1212. A spinal canal 1214 (i.e., an opening) is provided in the vertebra 1200. The spinal cord and nerves 1216 extend through the spinal canal 1214 such that the spinal cord 1216 receives the full protection of the bony, dorsally-located spinous, transverse, and mammillary processes and facet joints 1206, 1208, 1212. The vertebral body also protects the spinal cord and nerves 1216 ventrally. Periodically, nerves 1218 branch out from the spinal cord 1216 to innervate various areas of the body. The forward or ventral edge of the vertebral foramen 1221 is defined by the vertebral body (not shown in FIG. 2), a bony, generally elliptical shelf in front of which the intervertebral disc 1202 rests. FIG. 2 also illustrates the basic structure of the intervertebral disc 1202, including the annulus fibrosis 1222 and the nucleus pulposus 1224.

Figure 3:
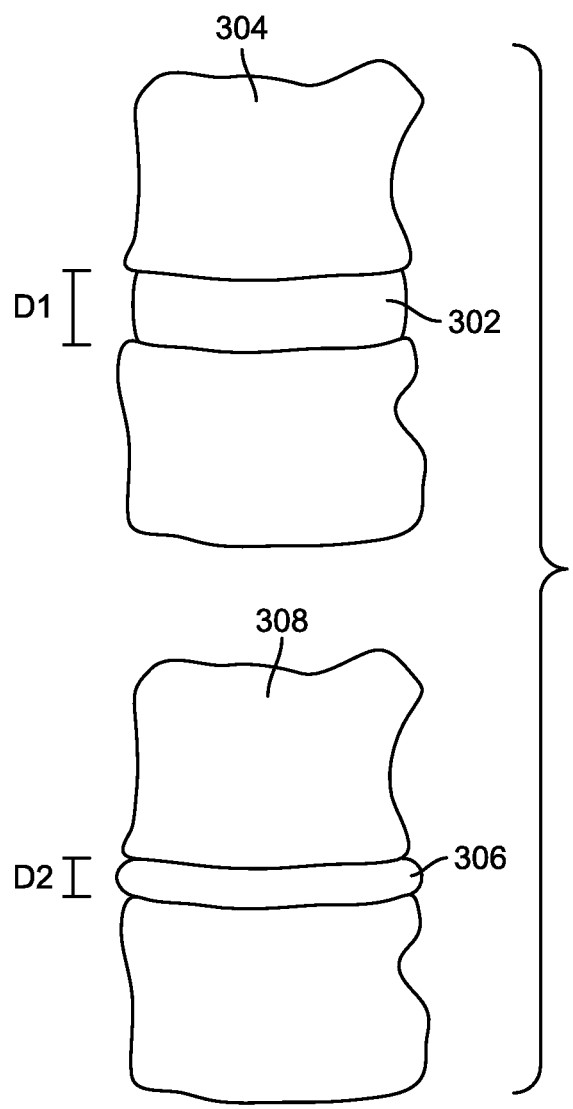
FIG. 3 is a schematic view of a preferred embodiment of a healthy intervertebral disc and an intervertebral disc that has degenerated.

In some cases, an intervertebral disc 1202 may degenerate over time, requiring the need for a spinal disc implant. FIG. 3 illustrates a preferred embodiment of degeneration. In this embodiment, healthy intervertebral disc 302 is disposed between vertebrae 304. In this case, vertebrae 304 are separated by a distance D1 because of support provided by disc 302. Also shown in FIG. 3 is unhealthy intervertebral disc 306, which is disposed between vertebrae 308. In this case, vertebrae 308 are separated by a distance D2 that is much smaller than distance D1 because of the degeneration of disc 306.

If an intervertebral disc has failed or degenerated, a typical correction is a surgical procedure to remove some or all of the intervertebral disc. Following this, a spinal prosthesis may be inserted in order to facilitate fusion of the vertebrae adjacent to the failed intervertebral disc. In a preferred embodiment, surgery may be performed in a manner that limits the size of the incisions needed to insert a prosthesis. Preferably, a spinal prosthesis includes provisions for easy insertion via a small incision in the back.

In some cases, a vertebral body could also be fully or partially replaced using a spinal prosthesis. The following detailed description refers to the replacement of an intervertebral disc, however in other embodiments these same principles could be applied to a spinal prosthesis configured to replace a vertebral body.

Figure 4:
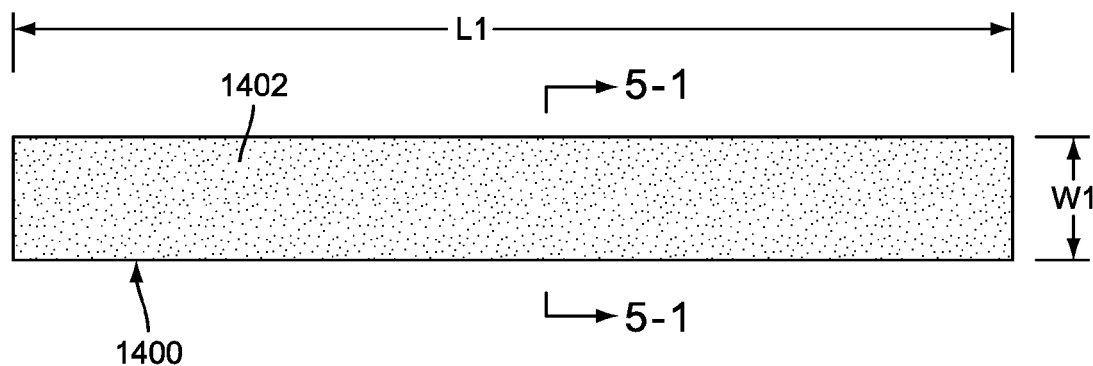
FIG. 4 is a plan view of a preferred embodiment of an implant strip.
Figures 1, 5:
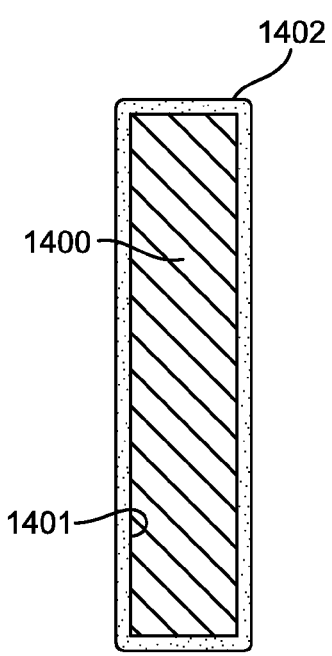
Figures 2, 5:
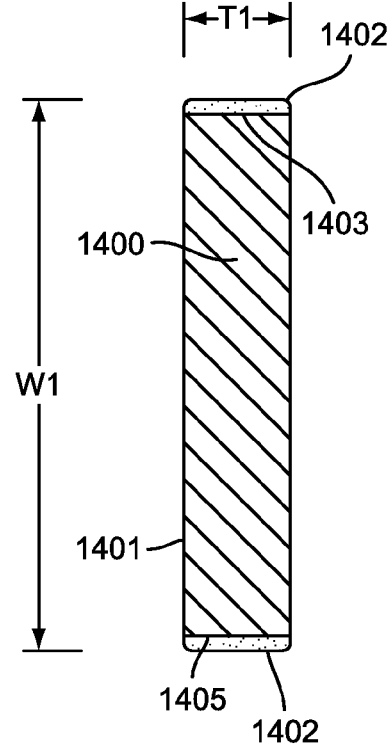

FIGS. 4 and 5 illustrate a preferred embodiment of implant strip 1400. Generally, implant strip 1400 may be a long thin strip. Preferably, implant strip 1400 has a length L1 much greater than a width W1. Additionally, the thickness T1 of implant strip 1400 is preferably small compared to both the length and the width of implant strip 1400. In some embodiments, length L1 may be between 1 cm and 100 m. In some embodiments, width W1 may be between 2 mm and 20 cm. In some embodiments, thickness T1 may be between 0.01 mm and 3 mm. It should be understood that if a vertebral body is being replaced, the thickness of implant strip 1400 could be much larger than the values discussed here.

As implant strip 1400 preferably has a relatively small profile, it may be inserted into smaller incisions, such as those shown in FIG. 1. However, to provide adequate support to the adjacent vertebrae, implant strip 1400 may preferably be packed tightly into intervertebral disc 1202. In some embodiments, the packing of implant strip 1400 may be tight or loose depending upon mechanical properties of implant strip 1400. For this reason, implant strip 1400 preferably includes provisions for conforming to a packed shape once it has been inserted into intervertebral disc 1202.

Generally, implant strip 1400 may be constructed of a material including metal. In some embodiments, implant strip 1400 may be a shape memory alloy. In some embodiments, implant strip 1400 may be made of a titanium alloy. In other embodiments, implant strip 1400 may comprise a combination of one or more materials including, but not limited to, cobalt chrome (CoCr), stainless steel, Nitinol, polymers, biological matrices, ceramics or any biocompatible material. In a preferred embodiment, implant strip 1400 may be made of a material including titanium.

In some cases, a stainless steel alloy may be used as a coiling spring. This arrangement is useful because such alloys low fatigue and high fatigue resistance. Additionally, these alloys may have a high return force. Additionally, using a stainless steel alloy allows for increased corrosion resistance.

Preferably, implant strip 1400 may include provisions for changing shape. In some embodiments, implant strip 1400 may be manufactured at an elevated temperature with a first shape. Following this, implant strip 1400 may be cooled and deformed into a second shape. Finally, as implant strip is placed in temperature ranges of 90-100 degrees Fahrenheit, it may deform back to the first shape. In a preferred embodiment, the first shape is a spiral coil and the second shape is a long rectangular strip.

In some embodiments, implant strip 1400 may include provisions for promoting bone growth, once it has been inserted into the intervertebral disc region. In some embodiments, implant strip 1400 may include a bone growth promoting agent. In a preferred embodiment, implant strip 1400 preferably includes bone growth promoting agent 1402 disposed along the entirety of its length. FIG. 5-1 is a cross sectional view of implant strip 1400 with bone growth promoting agent 1402 disposed along its entire outer surface 1401.

In some embodiments, bone growth promoting agent 1402 may be selectively applied to one or more portions of implant strip 1400 or may not be applied at all. Preferably, as shown in FIG. 5-2, bone growth promoting agent 1402 may be applied to top surface 1403 of outer surface 1401. Likewise, bone growth promoting agent 1402 may also be applied to bottom surface 1405 of outer surface 1401. Generally, any type of bone growth promoting agent may be applied and in any pattern. Methods for selectively applying bone growth promoting agents have been previously disclosed in U.S. Pat. No. 8,241,357, now U.S. patent application Ser. No. 11/740,181, the entirety of which is hereby incorporated by reference.

Figure 6:
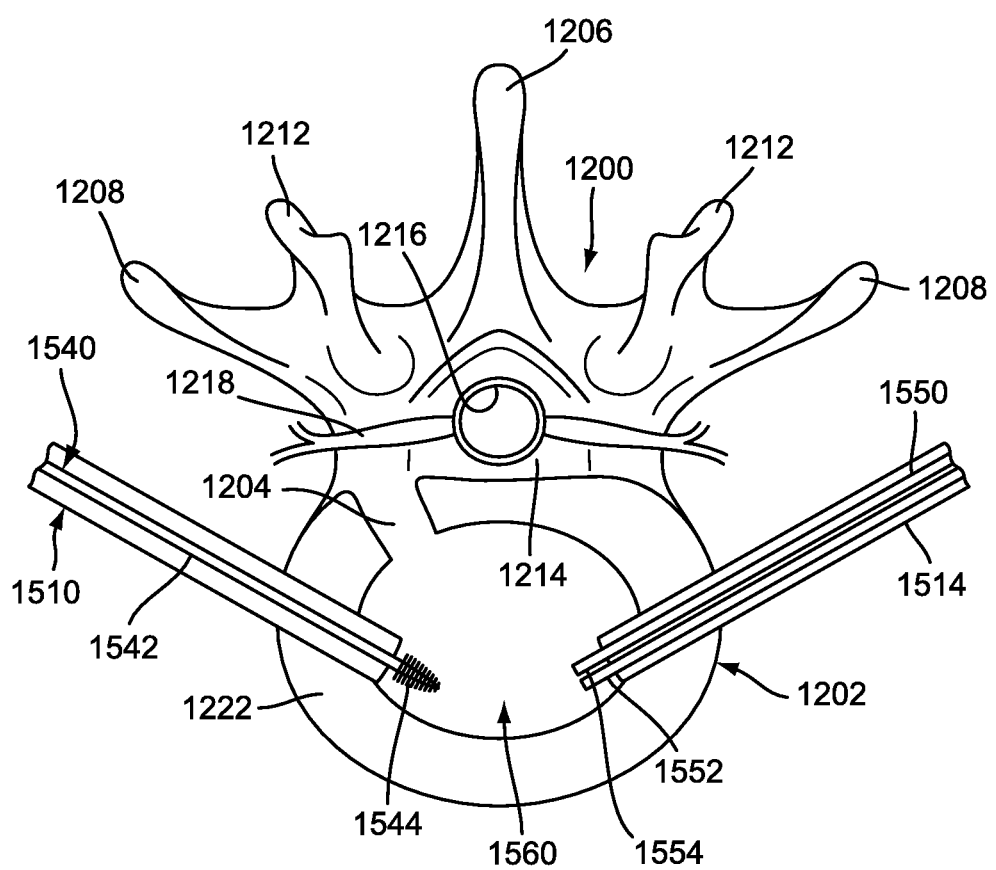
FIG. 6 is a plan view of a preferred embodiment of an intervertebral disc with a surgical tool and a dual catheter inserted.
Figure 7:
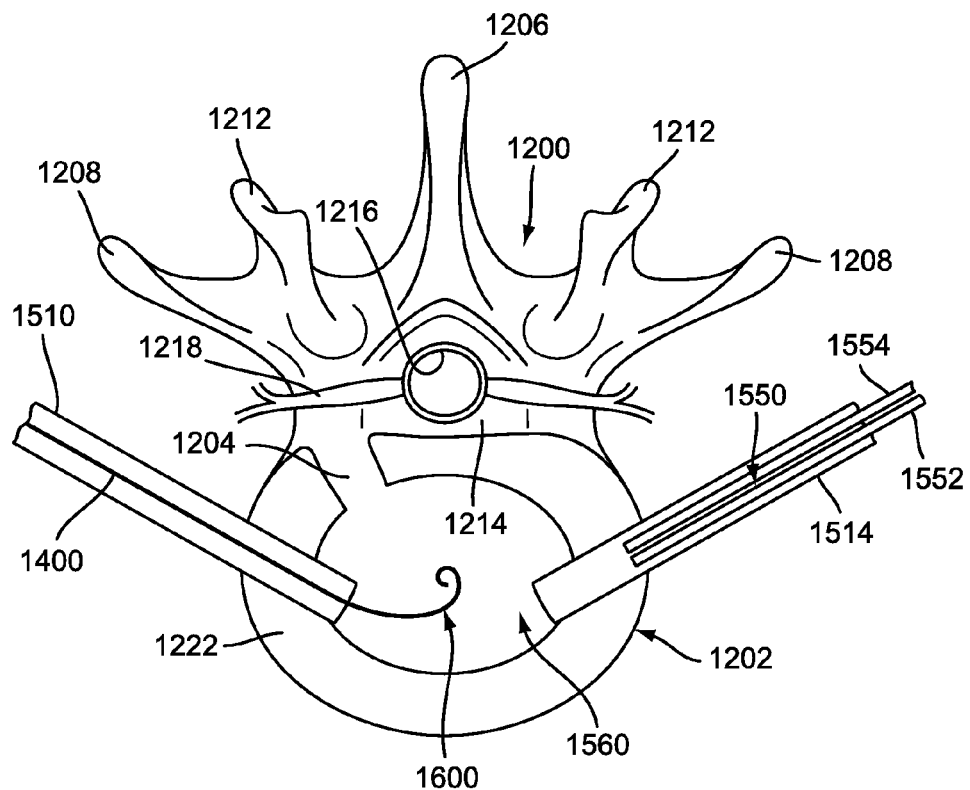
FIG. 7 is a plan view of a preferred embodiment of an intervertebral disc with an implant strip being inserted.
Figure 8:
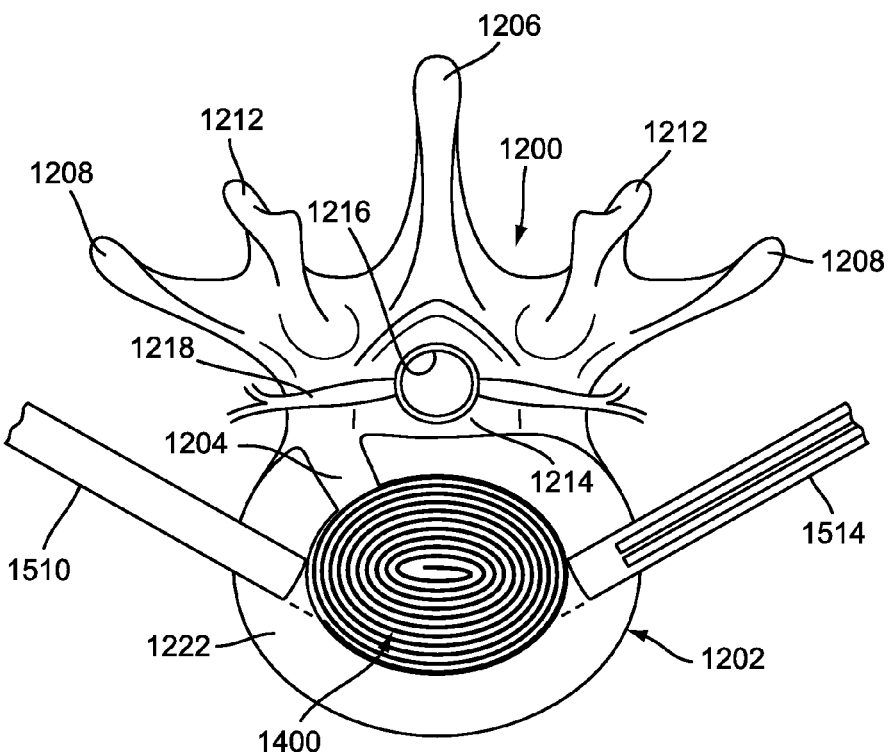
FIG. 8 is a plan view of a preferred embodiment of an implant strip fully inserted.

Details of a preferred embodiment of a surgical procedure used to insert a spinal prosthesis of some kind are best understood with respect to FIGS. 6-8. The following embodiment comprises steps for inserting a spinal prosthesis using two tubes, however it should be understood that in other embodiments, a single tube may be used for discectomy and/or implantation. In this case, any parallel steps involving the use of two tubes simultaneously could be performed sequentially with a single tube. In particular, steps using a camera and/or light inserted through one tube and a spinal tool through a second tube may be accomplished by using a single tube incorporating a light and/or camera at the periphery of the tube or just outside of the tube.

In a first step, first tube 1510 and second tube 1514 may be inserted into intervertebral disc 1202. Generally, one tube may be used for a surgical tool, while the second tube may be simultaneously used to insert a fiber optic camera into one of the incisions to give the surgeon a clear view of the intervertebral disc region. In some embodiments, first tube 1510 and second tube 1514 may be cannulae. The cross sectional shape of tubes 1510 and 1514 may be any shape, including oval-like, circular or otherwise round, as well as hexagonal or any polygonal shape.

Following the insertion of first tube 1510 and second tube 1514, a series of instruments may be used to remove portions of intervertebral disc 1202 and score the endplates. In some embodiments, first surgical device 1540 may be inserted into first tube 1510. First surgical device 1540 may be a brush, burr, rasp or a shaver. In a preferred embodiment, first surgical device 1540 may include flexible shaft 1542 and wire brush tip 1544. Preferably, wire brush tip 1544 spins, removing portions of intervertebral disc 1202.

In some embodiments, dual catheter 1550 may be inserted into second tube 1514. Preferably, dual catheter 1550 may include first channel 1552 and second channel 1554. In some embodiments, first channel 1552 may include a fiber optic camera. With this configuration, the surgery may be visualized by the surgeon using the fiber optic camera. Additionally, second channel 1554 may be configured to inject water and/or provide a vacuum for removing debris. With this configuration, second channel 1554 may be used to clean out cavity 1560, which is created as a portion of intervertebral disc 1202 is removed. Once the necessary portions of intervertebral disc 1202 have been removed, first surgical device 1540 may be removed from first tube 1510.

Referring to FIGS. 7-8, implant strip 1400 may be inserted into cavity 1560 once a portion of intervertebral disc 1202 has been removed. As previously discussed, implant strip 1400 preferably has a material structure that allows it to change shape following insertion into cavity 1560. In a preferred embodiment, implant strip 1400 is configured to coil as it is exposed to temperatures between 90 and 100 degree Fahrenheit. In other embodiments, implant strip 1400 could coil due to non-temperature dependent memory, such as occurs with a measuring tape. This could be achieved using a titanium implant strip, for example.

In this embodiment, first portion 1600 of implant strip 1400 has started to coil as it is inserted into cavity 1560. Preferably, as implant strip 1400 is further inserted through first tube 1510, the portion disposed within cavity 1560 may deform and coil as well. In a preferred embodiment, implant strip 1400 may be inserted in a manner that allows implant strip 1400 to coil around itself completely, as seen in FIG. 8.

Generally, implant strip 1400 may be configured to fill cavity 1560 of intervertebral disc 1202 completely. For illustrative purposes, implant strip 1400 is shown here to be coiled with large gaps between adjacent portions. However, in some embodiments, implant strip 1400 may be coiled tightly so that no gaps are seen. In a preferred embodiment, implant strip 1400 may be coiled loosely to provide space or gaps between adjacent, radially spaced coils. This arrangement may help to facilitate bone growth to occur between the coils.

In an alternative embodiment, multiple implant strips may be used. Preferably, each implant strip may include a coiled shape, similar to the shape of the previous embodiment. In some embodiments, each of the implant strips may be disposed against one another. In some embodiments, each of the implant strips may be associated with different heights in order to create lordosis.

Figure 9:
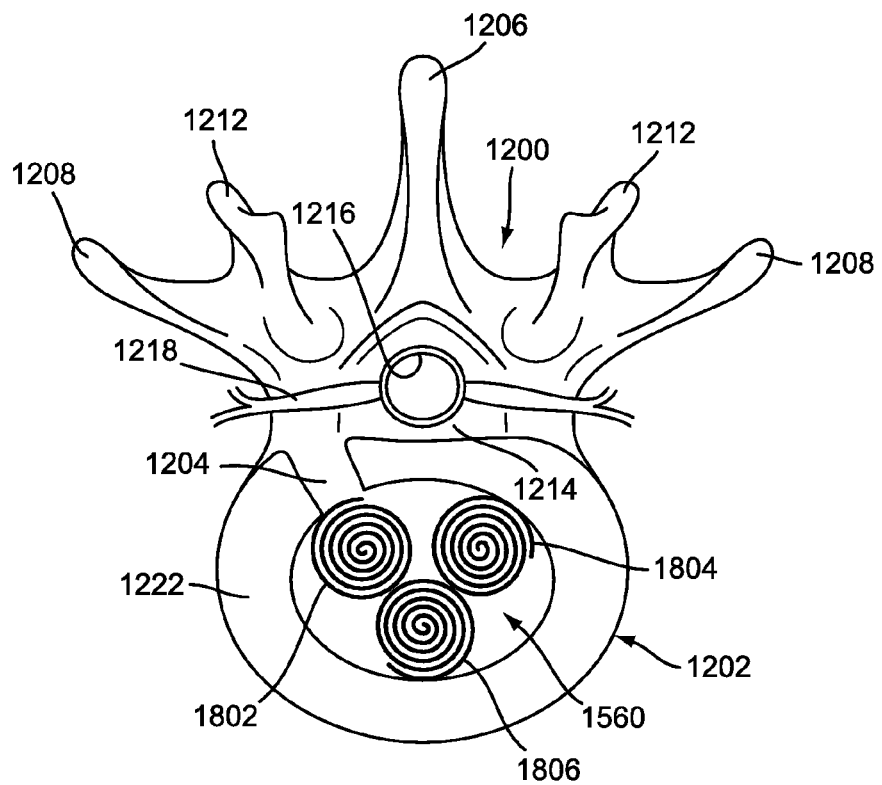
FIG. 9 is a plan view of a preferred embodiment of an intervertebral disc including three implant strips.

FIG. 9 is a preferred embodiment including multiple implant strips inserted within cavity 1560. In this embodiment, first implant strip 1802, second implant strip 1804 and third implant strip 1806 have been inserted into cavity 1560. Preferably, each of the implant strips 1802, 1804 and 1806 may be inserted in an identical manner to the method used to insert the implant strip of the previous embodiment. Generally, any number of implant strips may be inserted into cavity 1560.

Preferably, each of the implant strips 1802, 1804 and 1806 may be constructed of a shape memory alloy. In some embodiments, the shape memory alloy may be a nickel titanium alloy. In other embodiments, implant strips 1802, 1804 and 1806 may comprise a combination of one or more materials including, but not limited to, cobalt chrome (CoCr), stainless steel, Nitinol, polymers, biological matrices, ceramics or any biocompatible material. In a preferred embodiment, implant strips 1802, 1804 and 1806 may be made of a material including titanium.

In other embodiments, the structure of an implant strip may be modified. In some embodiments, an implant strip may include a slightly different shape. In other embodiments, an additional material may be used in conjunction with the shape memory alloy of the previous embodiments.

Figure 10:
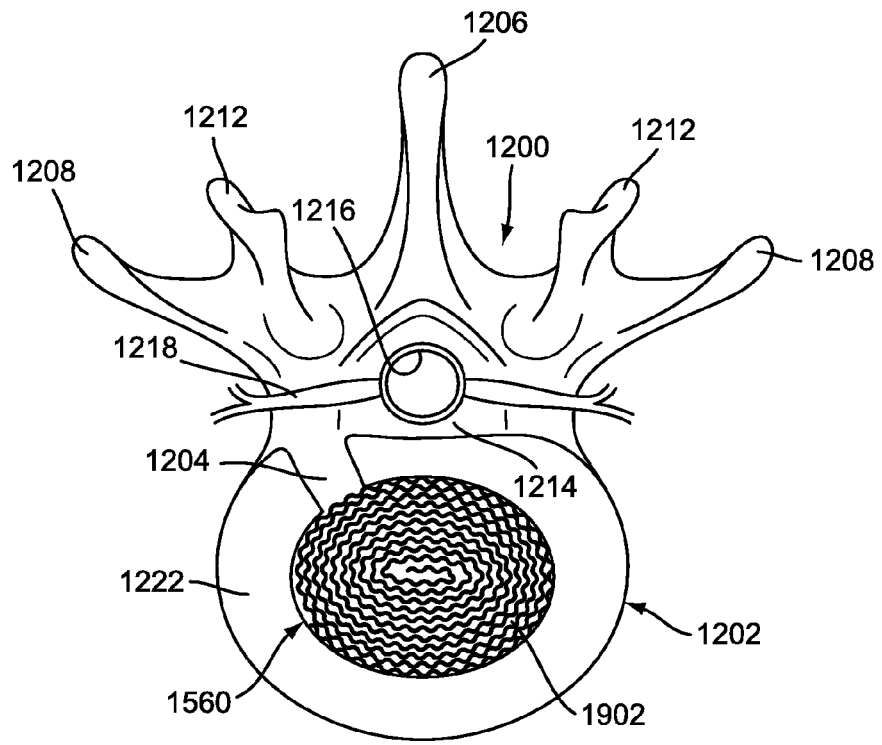
FIG. 10 is a plan view of a preferred embodiment of an intervertebral disc with a corrugated implant strip inserted.

FIG. 10 is a preferred embodiment of corrugated implant strip 1902, which has been inserted into cavity 1560. Preferably corrugated implant strip 1902 includes small bends along its length. Preferably, corrugated implant strip 1902 may be inserted into cavity 1560 in an identical manner to the method used to insert the previously discussed implant strips. As with the previous embodiments, it should be understood that a bone growth promoting agent may be applied to corrugated implant strip 1902. This arrangement allows for greater mechanical strength as well as for facilitating increased bone growth into implant strip 1902. By providing increased surface area, this arrangement may facilitate greater bone growth and more rapid bone healing.

Preferably, corrugated implant strip 1902 may be constructed of a shape memory material. In some embodiments, the shape memory alloy may be a nickel titanium alloy. In a preferred embodiment, corrugated implant strip 1902 may be made of a material including titanium. Generally, corrugated implant strip 1902 may be made of any of the materials discussed with respect to the previous embodiments of implant strips, including cobalt chrome (CoCr), stainless steel, Nitinol, polymers, biological matrices, ceramics or any biocompatible material.

Preferably, an implant device includes provisions for allowing for different kinds of motion that may occur in a spine.

In some embodiments, an implant device may include provisions to accommodate deflections in the axial direction. This may be a useful feature as axial forces may be applied to the implant strip by the adjacent vertebrae during normal activities such as walking, running and bending of the spinal column. In other words, the implant strip may be configured to endure axial loads that are usually applied to spinal discs. Additionally, the implant device may be configured to accommodate bending, lateral (including shear forces), and twisting forces.

FIGS. 11-14 are intended to illustrate a generic embodiment of implant device 2200. Generally, implant device 2200 may be any kind of device configured for implantation into the human body. In some cases, implant device 2200 may be configured to be implanted between vertebrae, functioning as a full or partial disc replacement device. In a preferred embodiment, implant device 2200 may be an implant strip.

Figure 11:
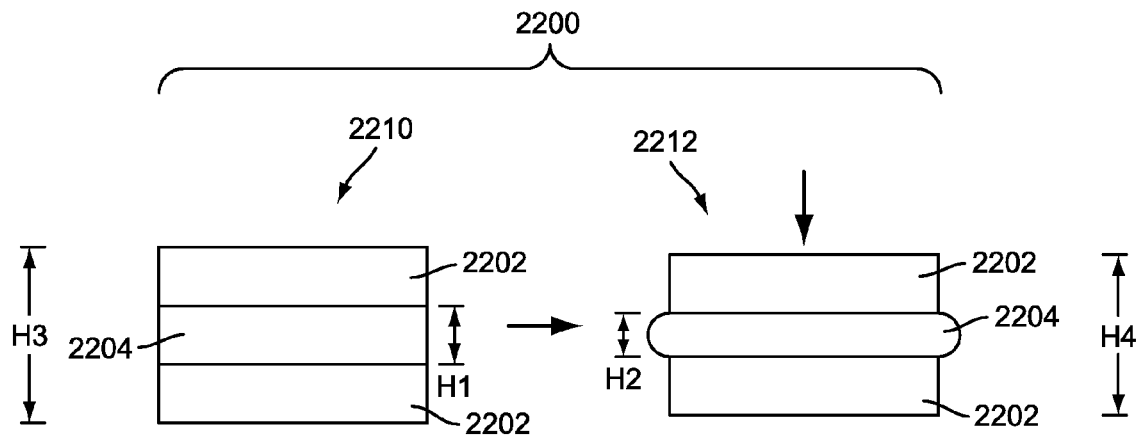
FIG. 11 is a schematic view of a preferred embodiment of an implant device in a pre-deflection state and a post-deflection state.

FIG. 11 is intended to illustrate a general embodiment of implant device 2200 in a pre-deflection state 2210 and a post-deflection state 2212. In this embodiment, implant device 2200 includes first portion 2202 and second portion 2204. Preferably, first portion 2202 is relatively rigid compared to second portion 2204. In other words, second portion 2204 is configured to deflect under axial forces before first portion 2202 would deflect. As shown in FIG. 11, second portion 2204 has a first height H1 in a pre-deflection state 2210 and a second height H2 in a post-deflection state 2212. First height H1 is preferably greater than second height H2. Additionally, first portion 2202 and second portion 2204 have a third combined height H3, in pre-deflection state 2210 and a fourth combined height H4 in post-deflection state 2212. Third combined height H3 is preferably greater that fourth combined height H4. This preferred arrangement allows for some deflection of implant device 2200 without causing fatigue or failure.

Figure 12:
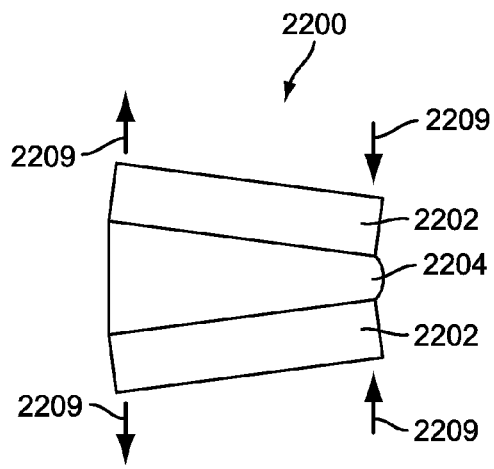
FIG. 12 is a schematic view of a preferred embodiment of an implant device undergoing bending.

In addition to deflection in the axial direction, a spinal implant device may also be configured to undergo bending, lateral and twisting motions. Implant device 2200 is seen in FIG. 12 to undergo a bending motion due to bending forces 2209. As bending forces 2209 are applied to first portion 2202, second portion 2204 may bend. This preferred arrangement allows for some bending of implant device 2200 without causing fatigue or failure.

Figure 13:
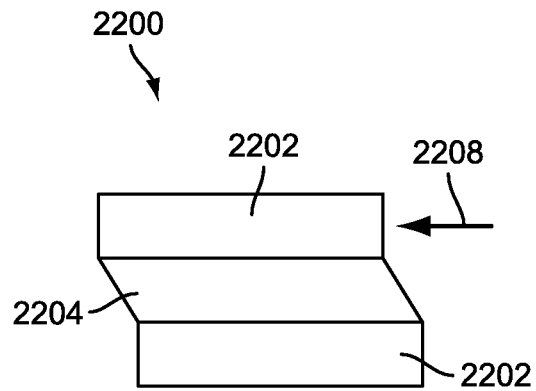
FIG. 13 is a schematic view of a preferred embodiment of an implant device undergoing translation.

Implant device 2200 is seen in FIG. 13 undergoing a lateral motion due to a lateral force 2208. As lateral force 2208 is applied to first portion 2202, second portion 2204 may be deflected laterally. This preferred arrangement allows for some lateral deflection of implant device 2200 without causing fatigue or failure.

Figure 14:
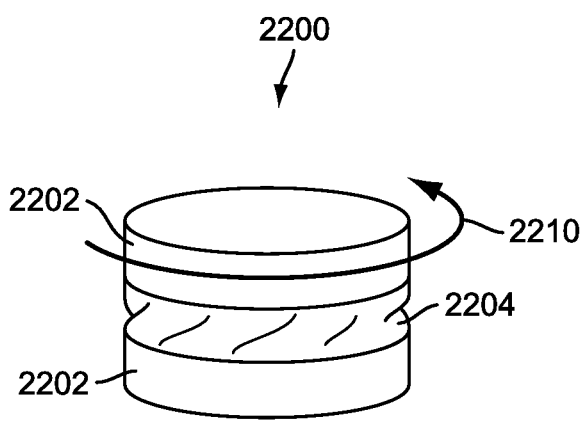
FIG. 14 is a schematic view of a preferred embodiment of an implant device undergoing twisting.

Referring to FIG. 14, implant device 2200 is seen in undergoing a twisting motion due to a rotational force 2210. As rotational force 2210 is applied to first portion 2202, second portion 2204 may be twisted. This preferred arrangement allows for some twisting of implant device 2200 without causing fatigue or failure.

In each of these cases, first implant devices 2200 is provided with restoring forces via second portion 2204. Additionally, although these different types of deflections (due to compressive, bending, twisting and lateral forces) have been shown separately, it should be understood that implant device 2200 may be configured to undergo any combination of or all of these various types of deformations simultaneously.

First portion 2202 may be made of any material, including both shape memory alloys and spring steel, as well as other types of materials, including previously discussed materials for implant strip 1400. Second portion 2204 may be made of any material that may be less rigid than first portion 2202. In addition, second portion 2204 may be designed to deflect and/or deform under various forces. Examples of such materials include, but are not limited to, elastomers, soft metals, plastics, polymers, wire meshes (made from materials such as Dacron or ceramics), as well as other types of materials.

Additionally, in some embodiments, first portion 2202 and second portion 2204 could be made of the same material. However, the rigidity of second portion 2204 could be modified by changing the structural properties of second portion 2204. This configuration may be achieved by inserting holes or slots or modifying the structure of second portion 2204 in other ways. With these types of modifications, first portion 2202 may be more rigid than second portion 2204 even though they are made of the same material.

Preferably, the degree of deflection of implant device 2200 may vary. During the initial implantation, implant device 2200 may deflect or compress until the height of the implant device is about eighty percent of the initial height of the implant strip prior to implantation. This initial deflection is primarily due to normal stresses applied by the adjacent vertebrae when the spinal column is at rest. During motion, however, implant device 2200 may continue to deflect due to increased axial loads from the adjacent vertebrae. The degree of deflection may be between 15 and 25 percent of the initial height of implant device 2200. It should be understood, however, that the degree of deflection is not limited and may vary according to properties of the various materials that are used. In some cases, the degree of deflection could be much larger than 25 percent or much less that 15 percent. By carefully selecting the material, size, design as well as other structural features of second portion 2204, the deflection of implant device 2200 can be better controlled. The following embodiments illustrate ways in which the deflection of implant device 2200 can be achieved using different materials and structural features for second portion 2204.

Figure 15:
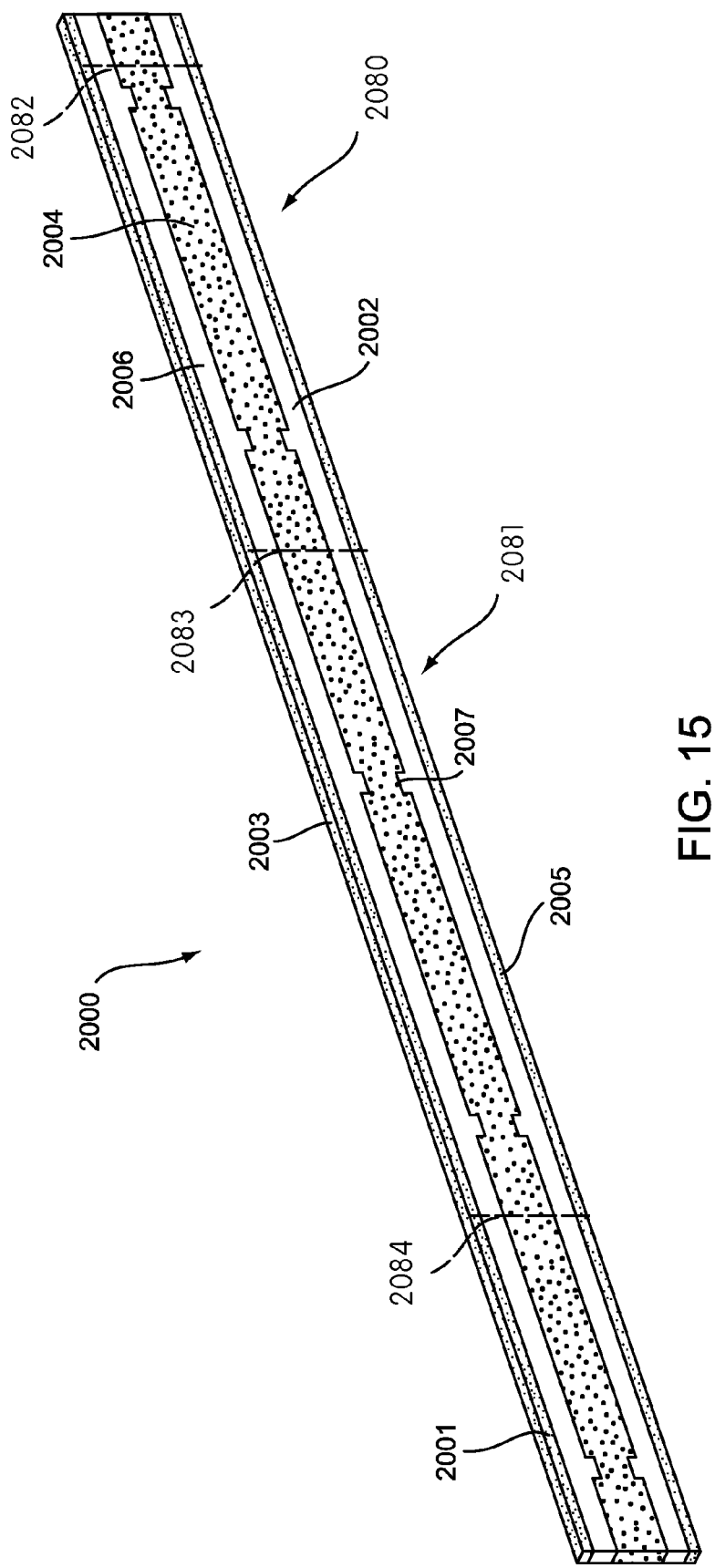
FIG. 15 is an isometric view of a preferred embodiment of an implant strip.

FIG. 15 is an isometric view of a preferred embodiment of implant strip 2000. In some embodiments, implant strip 2000 may extend in a lateral direction from a first lateral side portion 2002 to a second lateral side portion 2006. Preferably, first lateral side portion 2002 and second lateral side portion 2006 may be constructed of a similar material to the implant strips of the previous embodiments. In particular, side portions 2002 and 2006 may be made of a substantially rigid material that does not deflect much under axial loads.

In some embodiments, elastomer strip 2004 may be disposed between first lateral side portion 2002 and second lateral side portion 2006. Elastomer strip 2004 is preferably made of a flexible material. In some embodiments, elastomer strip 2004 may be joined to first lateral side portion 2002 and second lateral side portion 2006. In some embodiments, elastomer strip 2004 may encase perforated edges, teeth or roughed edges of first lateral side portion 2002 and second lateral side portion 2006 in order to ensure a positive mechanical connection. In this preferred embodiment, first lateral side portion 2002 and second lateral side portion 2206 may be associated with teeth 2007. Using this configuration, teeth 2007 provide a point of attachment for elastomer strip 2004 to first lateral side portion 2002 and second lateral side portion 2006. In other embodiments, other provisions may be used to fixedly attach elastomer strip 2004 to first lateral side portion 2002 and second lateral side portion 2006.

In some embodiments, implant strip 2000 may include a bone growth promoting agent. In this embodiment, top portion 2003 and bottom portion 2005 are preferably coated with a bone growth promoting agent 2001. Generally, any type of bone growth promoting agent may be used. Additionally, any type of pattern for a bone growth promoting agent may be used. Various bone growth promoting agents and patterns have been previously referenced. Using this configuration, implant strip 2000 may be configured to stimulate increased bone growth at adjacent vertebrae where implant strip 2000 is implanted. In some embodiments, such a configuration may be used in a manner similar to a spinal cage, which provides a means of fusing two vertebral bodies together.

Figure 16:
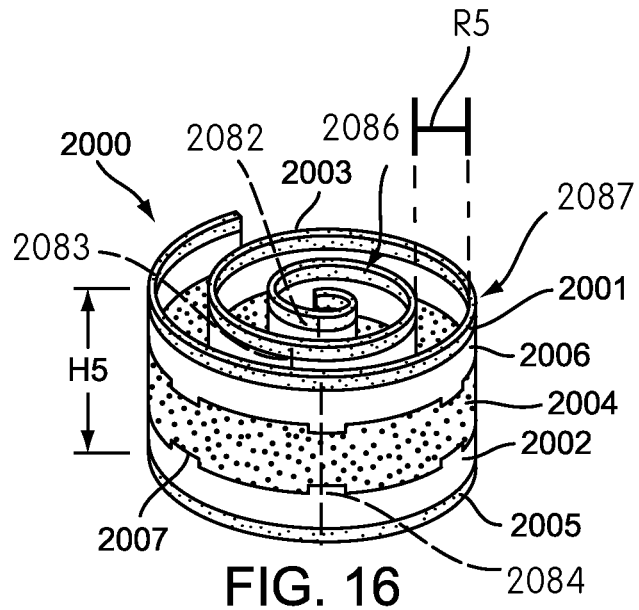
FIG. 16 is an isometric view of a preferred embodiment of an implant strip that has coiled.
Figure 17:
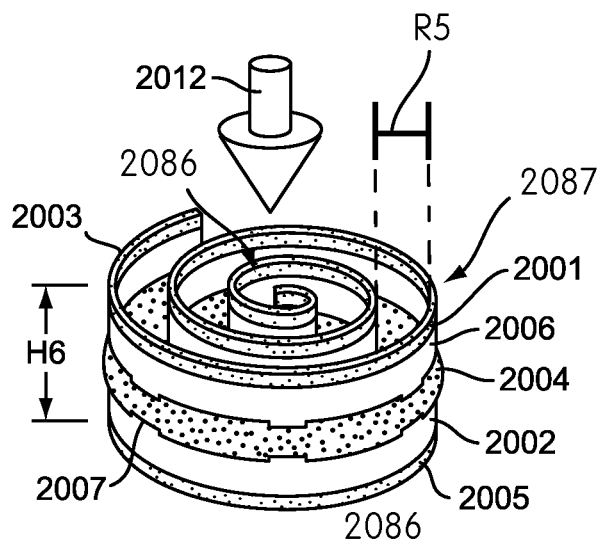
FIG. 17 is an isometric view of a preferred embodiment of a coiled implant strip under axial force.

FIGS. 16 and 17 are a preferred embodiment of implant strip 2000 after it has been coiled. Initially, implant strip 2000 has an axial height H5. As axial force 2012 is applied to flexible implant strip 2000, elastomer strip 2004 may deflect in the axial direction, allowing first lateral side portion 2002 and a second lateral side portion 2006 to squeeze together. In this embodiment, flexible implant strip 2000 has a height H6 that is less than height H5 following axial deflection. Generally, elastomer strip 2004 has deformed and may slightly bulge outwards. This preferred arrangement allows implant strip 2000 to deflect under axial forces applied by adjacent vertebrae following implantation, which provides a similar function to a spinal disc. Also, using this configuration flexible implant strip 2000 may be configured as a flexible spiral coil that may not escape containment. Preferably, using this arrangement, the adjacent vertebrae may engage lateral side portions 2002 and 2006 of implant strip 2000 to lock it into place.

Referring to FIGS. 15-17, implant strip 2000 preferably is configured to be coiled in a manner that prevents contact between adjacent coils. In this embodiment, implant strip 2000 may include first longitudinal portion 2080 and second longitudinal portion 2081 extending in a longitudinal direction down the length of implant strip 2000, as seen in FIG. 15. First longitudinal portion 2080 extends from first boundary 2082 to second boundary 2083. Second longitudinal portion 2081 extends from second boundary 2083 to third boundary 2084. Generally, the lengths of each longitudinal portion 2080 and 2081 are approximately equal to one 360 degree turn of a coil when implant strip 2000 is in a coiled state. In this embodiment, longitudinal portions 2080 and 2081 are adjacent to one another, however in other embodiments longitudinal portions 2080 and 2081 may not be adjacent to one another.

Preferably, first longitudinal portion 2080 is configured to form a first inner coil 2086, as seen in FIGS. 15-17, as implant strip 2000 deforms to a coiled shape. Likewise, second longitudinal portion 2081 is configured to form a second outer coil 2087. In a preferred embodiment, second outer coil 2087 is spaced radially outward from first inner coil 2086. In some embodiments, first inner coil 2086 and second outer coil 2087 are spaced apart by a radial distance R5 when first lateral side portion 2002 and second lateral side portion 2006 are not in motion (see FIG. 16). Generally, distance R5 may have any value and may vary from one embodiment to another. Using this preferred arrangement, first inner coil 2086 and second outer coil 2087 are spaced to prevent contact with one another. Preferably, first inner coil 2086 and second outer coil 2087 are also spaced apart when first lateral side portion 2002 and second lateral side portion 2006 are in motion, such as when implant strip 2000 is in a compressed or axially deflected state (see FIG. 17). This arrangement helps to reduce or substantially eliminate particulate debris that may result from the rubbing of various portions together over the lifetime of implant strip 1400.

Preferably, provisions for preventing contact between portions of an implant strip may be provided in other embodiments as well. The principles discussed here may be generally applied to any type of implant strip including a first longitudinal portion and a second longitudinal portion. In some embodiments, these implant strips may or may not include deforming portions.

In other embodiments, an implant strip may include different provisions for allowing deflection of the implant strip in the axial direction. In some embodiments, an implant strip may include perforated portions with large gaps or holes that reduce rigidity and thereby allow for some deflection of the implant strip. It should be understood that throughout these embodiments, illustrated in FIGS. 18-34, the various implant strips include portions of differing rigidity. Furthermore, in each of these embodiments, the portions of differing rigidity are joined together.

FIGS. 18-25 are preferred embodiments of sections of spinal implant strips that are configured for various types of deflection, including axial deflection. The spinal implant strips are also capable of accommodating other types of deflection, including bending, twisting and lateral shear. Throughout these embodiments, it should be understood that the implant strips may be made of any material configured to coil or deflect in the circumferential direction. In some embodiments, these sections of implant strips may be made of a single material or comprise a combination of one or more materials including, but not limited to, cobalt chrome (CoCr), stainless steel, Nitinol, polymers, biological matrices, ceramics or any biocompatible material. In a preferred embodiment, these sections of implant strips may be made of a material including titanium.

Figure 18:
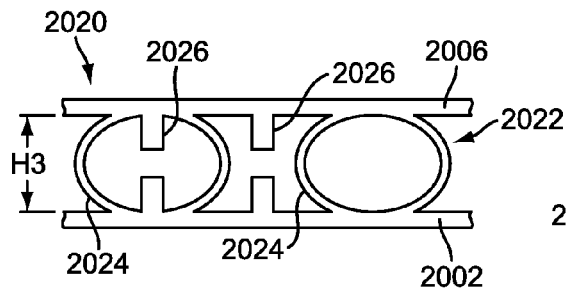
FIG. 18 is a plan view of a preferred embodiment of a section of an implant strip configured for axial deflection.

FIG. 18 is a preferred embodiment of a portion of first implant strip 2020 prior to deflection. First implant strip 2020 preferably includes lower edge 2002 and upper edge 2006. Lower edge 2002 and upper edge 2006 are preferably thin strips that form an outer periphery for first implant strip 2020.

Additionally, first implant strip 2020 may include first deflecting portions 2024 that are disposed between lower edge 2002 and upper edge 2006. Preferably, lower edge 2002 and upper edge 2006 are joined to first deflecting portions 2024. For purposes of clarity, only a section of first implant strip 2020 is shown here, however it should be understood that first deflecting portions 2024 are preferably disposed along the entire length of first implant strip 2020. Generally, the spacing and number of first deflecting portions 2024 may be varied in order to change the deflection properties of first implant strip 2020.

In this embodiment, first deflecting portions 2024 may be elliptically shaped prior to deflection. In other embodiments, the shape of first deflecting portions 2024 may vary. Examples of other shapes that may be used include, but are not limited to, circles, diamonds, as well as any polygonal shape. Additionally, in other embodiments, the thickness associated with first deflecting portions 2024 could be changed. By varying these properties of first deflecting portions 2024, the deflection properties of first implant strip 2020 may be modified.

In some embodiments, first implant strip 2020 may also include motion limiting features that prevent excessive deflection in the axial direction. In this embodiment, first implant strip 2020 may include motion limiting tabs 2026. Preferably, motion limiting tabs 2026 may be disposed between edges 2002 and 2006. Furthermore, motion limiting tabs 2026 may be disposed within deflecting portions 2024 and/or adjacent to deflecting portions 2024.

Preferably, deflecting portions 2024 and motion limiting tabs 2026 may be formed by cutting or removing portions of first implant strip 2020, which creates gaps within interior space 2022. This cutting may be done using techniques known in the art, such as stamping, punching, laser fusion and/or water drilling, or any combination of techniques. In other embodiments, first implant strip 2020, including deflecting portions 2024 and tabs 2026 may be formed using a die of some kind. These techniques are preferably used to create smooth edges in order to prevent burrs. Using this configuration, scar tissue due to burrs may be substantially reduced following implantation of first implant strip 2020. In other embodiments, however, techniques used that leave burrs intact may be used so that the remaining burrs may facilitate in-growth of bone.

Figure 19:
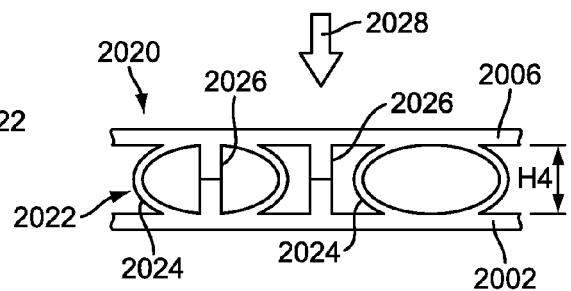
FIG. 19 is a plan view of a preferred embodiment of a section of an implant strip under axial load.
Figure 20:
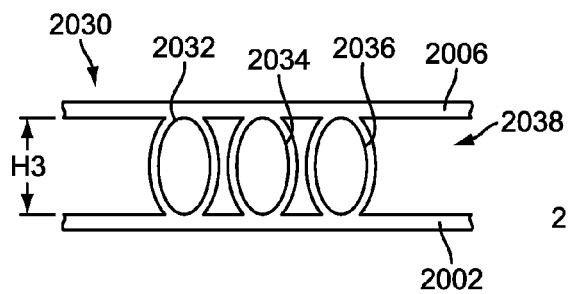
FIG. 20 is a plan view of a preferred embodiment of a section of an implant strip configured for axial deflection.
Figure 21:
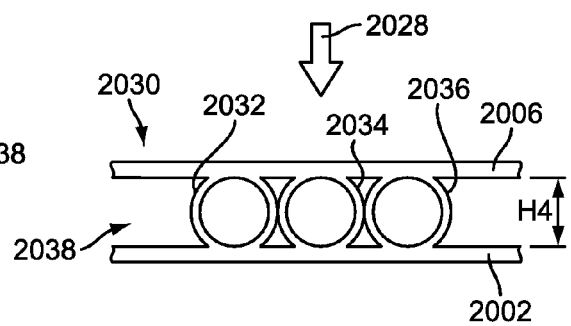
FIG. 21 is a plan view of a preferred embodiment of a section of an implant strip under axial load.

Following the insertion of first implant strip 2020 between two adjacent vertebrae, an axial force may be experienced as the vertebrae are compressed during motion of the spinal column. Referring to FIG. 19, first deflecting portions 2024 may be compressed under axial force 2028. As first deflecting portions 2024 compress, lower edge 2002 and upper edge 2006 move closer together. As previously discussed, excessive axial deflection may be prevented using motion limiting tabs 2026. Preferably, tabs 2026 are substantially rigid and therefore will not deflect or deform under axial force 2028. Therefore, as tabs 2026 make contact, the compression of first deflecting portions 2024 may cease. In this embodiment, the height of implant strip 2020 has been modified from an original height H3 to a modified height H4 that is less than H3. Once axial force 2028 has been removed or reduced, implant strip 2020 may expand in the axial direction as deflecting portions 2024 uncompress. Using tabs 2026 helps to prevent fatigue failure of deflecting portions 2024 by limiting the range of motion.

Referring to FIGS. 20-25, an implant strip may include different types of deflecting portions. Additionally, an implant strip may or may not include motion limiting tabs. In a second embodiment, seen in FIGS. 20-21, second implant strip 2030 includes first deflecting ellipse 2032, second deflecting ellipse 2034 and third deflecting ellipse 2036 disposed between edges 2002 and 2006 and within interior space 2038. Preferably, ellipses 2032, 2034 and 2036 are joined to edges 2002 and 2006. As axial force 2028 is applied, deflecting ellipses 2032, 2034 and 2036 are compressed until they obtain a substantially circular shape. At this point, ellipses 2032, 2034 and 2036 are disposed against one another, which may prevent any further deflection or deformation in the axial direction.

Figure 22:
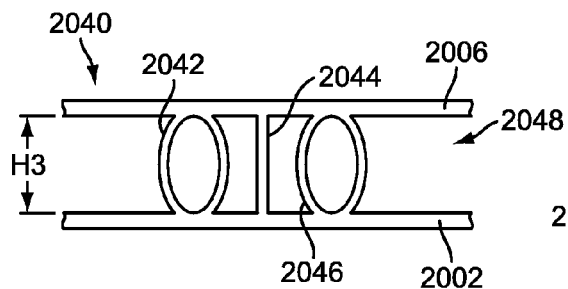
FIG. 22 is a plan view of a preferred embodiment of a section of an implant strip configured for axial deflection.
Figure 23:
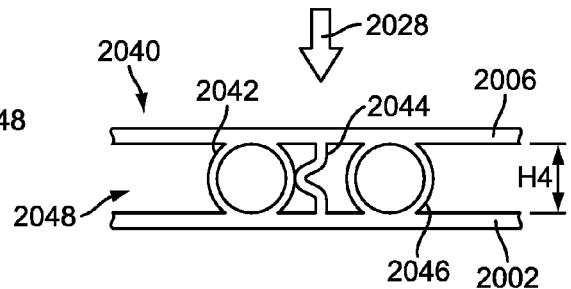
FIG. 23 is a plan view of a preferred embodiment of a section of an implant strip under axial load.

In a third embodiment, shown in FIGS. 22-23, third implant strip 2040 includes fourth deflecting ellipse 2042 and fifth deflecting ellipse 2046 disposed between edges 2002 and 2006 and within interior space 2048. Preferably, ellipses 2042 and 2046 are joined to edges 2002 and 2006. In addition, third implant strip 2040 preferably includes cross bar 2044 that is disposed between fourth deflecting ellipse 2042 and fifth deflecting ellipse 2046. Cross bar 2044 preferably connects to both lower edge 2002 and upper edge 2006. In a preferred embodiment, deflecting ellipses 2042 and 2046 as well as cross bar 2044 may all deflect under axial force 2028. In particular, cross bar 2044 may experience column deflection. Preferably, cross bar 2044 only partially deflects, which limits the axial motion of lower edge 2002 and upper edge 2006.

Figure 24:
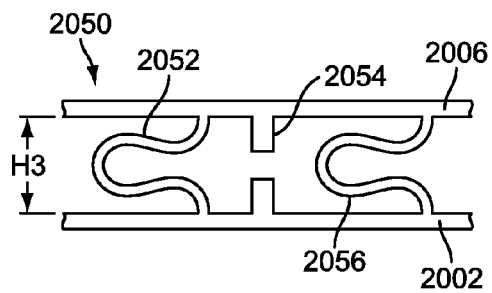
FIG. 24 is a plan view of a preferred embodiment of a section of an implant strip configured for axial deflection.
Figure 25:
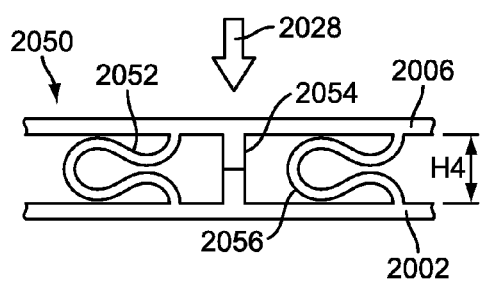
FIG. 25 is a plan view of a preferred embodiment of a section of an implant strip under axial load.

In a fourth embodiment, seen in FIGS. 24-25, fourth implant strip 2050 includes first curved portion 2052 and second curved portion 2056. Preferably, curved portions 2052 and 2056 are joined to edges 2002 and 2006. Fourth implant strip 2050 also preferably includes motion limiting tabs 2054. As axial force 2028 is applied to fourth implant strip 2050, curved portions 2052 and 2056 may deflect in the axial direction. Preferably, as tabs 2054 make contact, the deflection of lower edge 2002 towards upper edge 2006 may cease. Additionally, curved portions 2052 and 2056 may contact edges 2002 and 2006, preventing further deflection.

Figure 26:
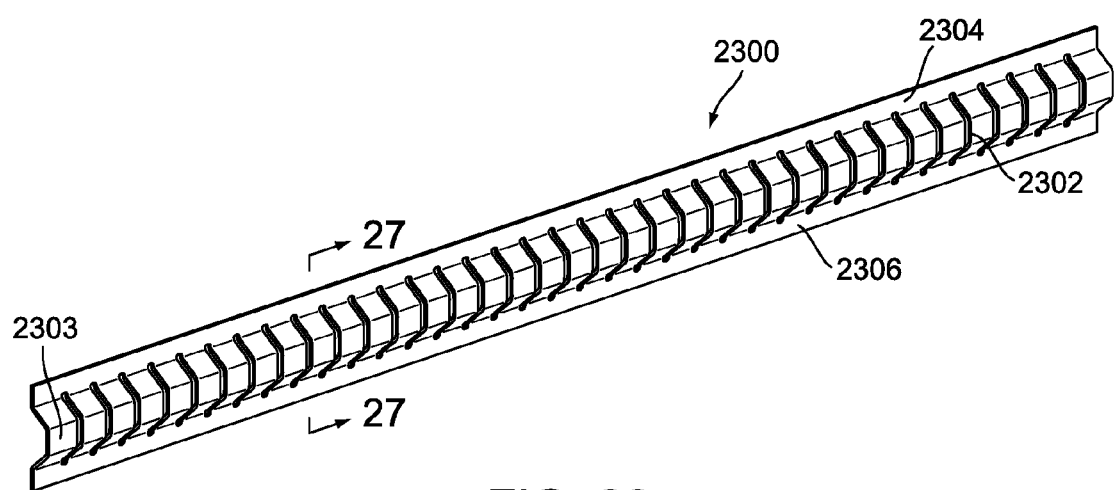
FIG. 26 is an isometric view of a preferred embodiment of an implant strip with slots.
Figure 27:
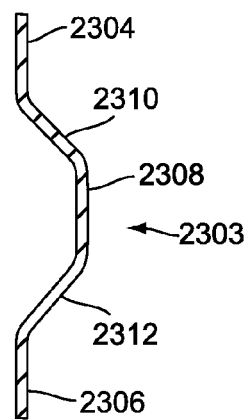
FIG. 27 is a cross sectional view of a preferred embodiment of an implant strip with slots.
Figure 28:
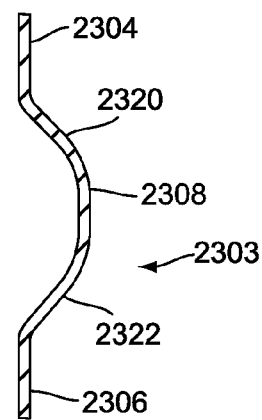
FIG. 28 is a cross sectional view of a preferred embodiment of an implant strip with slots.

FIGS. 26-28 illustrate another preferred embodiment of implant strip 2300 that is configured for axial deflection. Implant strip 2300 includes upper side 2304 and lower side 2306 that extend vertically. Protruding portion 2303 preferably extends outwards from, and is preferably joined with, upper side 2304 and lower side 2306. In particular, protruding portion 2303 includes first sloped portion 2310 and second sloped portion 2312 as well as flat portion 2308. Using this preferred arrangement, implant strip 2300 may be configured for slight deflections in the axial direction, as some slight compression of implant strip 2300 may occur at protruding portion 2303. In particular, as axial loads are applied to implant strip 2300, the angle of first sloped portion 2310 and second sloped portion 2312 with respect to upper side 2304 and lower side 2306 may vary.

FIG. 28 illustrates an alternative embodiment of a cross sectional view of protruding portion 2303. In the embodiment shown in FIG. 27, first sloped portion 2310 and second sloped portion 2312 are straight portions. Alternatively, protruding portion 2303 could include first curved portion 2320 and second curved portion 2322. Using an alternative shape for protruding portion 2303 allows for changes in the deflecting properties of implant strip 2300. In other embodiments, the shape of protruding portion 2303 could be further modified to change the deflecting properties of implant strip 2300.

Implant strip 2300 also preferably includes slots 2302. In this embodiment, slots 2302 extend from upper side 2304 to lower side 2306 of implant strip 2300. Slots 2302 preferably extend through protruding portion 2303. The addition of slots 2302 to implant strip 2300 generally decreases the rigidity of protruding portion 2303. Using this configuration, slots 2302 may provide increased deflection of protruding portion 2303.

Figure 29:
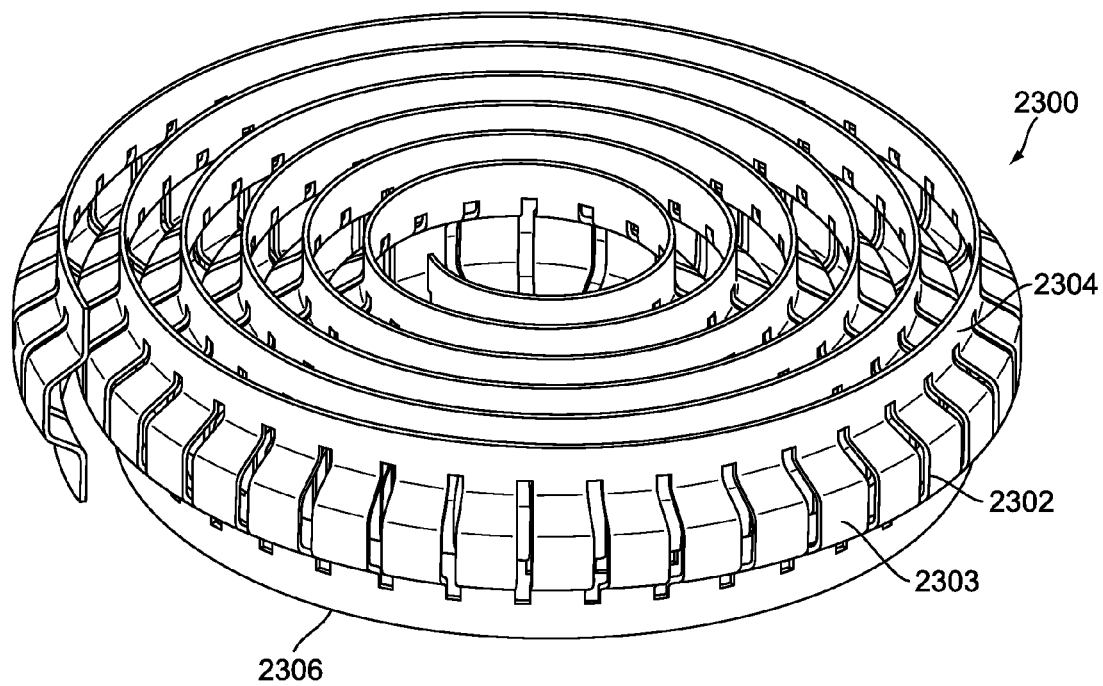
FIG. 29 is an isometric view of a preferred embodiment of a coiled implant strip with slots.
Figure 30:
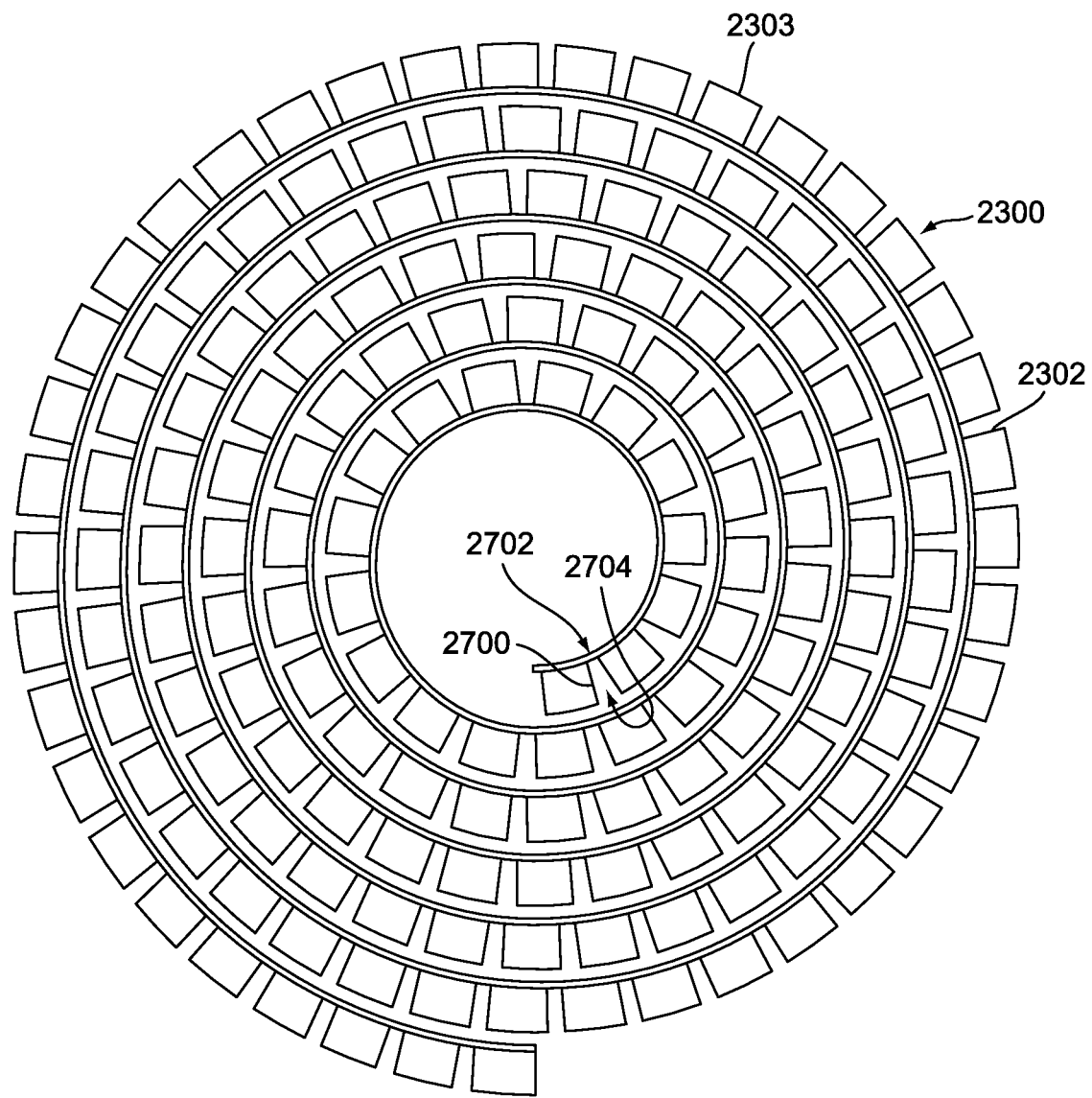
FIG. 30 is a top view of a preferred embodiment of a coiled implant strip with slots.

FIGS. 29 and 30 are a preferred embodiment of implant strip 2300 following implantation. As implant strip 2300 is coiled, implant strip 2300 is configured to deflect in the circumferential direction. In a preferred embodiment, the deflection primarily occurs at slots 2302. FIG. 30 illustrates the widening of slots 2302 during coiling. For example, first slot 2700 of implant strip 2300 is wider at first end 2704 than second end 2702.

Figure 31:
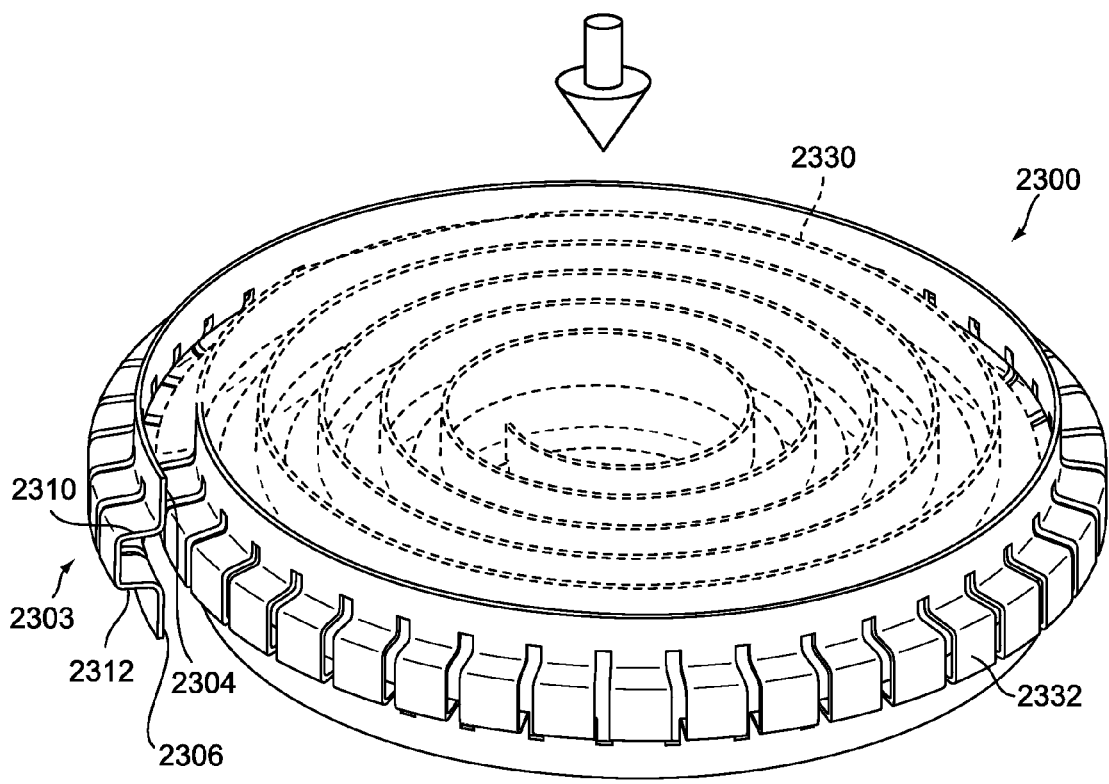
FIG. 31 is an isometric view of a preferred embodiment of an implant strip undergoing axial deflection.

FIG. 31 is a preferred embodiment of outer ring 2332 of implant strip 2300 undergoing axial deflection. For purposes of clarity, inner rings 2330 of implant strip 2300 are shown in phantom. As an axial force is applied, protruding portion 2303 deflects. In particular, the angle between upper side 2304 and first sloped portion 2310 and the angle between lower side 2306 and second sloped portion 2312 may change as upper side 2304 and lower side 2306 are squeezed together.

In some embodiments, the number, shape and size of slots associated with an implant strip may vary. By changing the number, shape, orientation and/or size of slots of an implant strip, the axial loading characteristics of the implant strip may be controlled. Increasing the number of slots may increase the degree of axial deflection, as the rigidity of protruding portion 2303 is reduced with an increasing number of slots. Likewise, decreasing the number of slots may decrease the degree of axial deflection, as the rigidity of protruding portion 2303 is increased with a decreased number of slots.

Additionally, changing the number of slots may also increase the flexibility of the implant strip in the circumferential direction. Increasing the number of slots may generally increase the amount of deflection in the circumferential direction. Likewise, decreasing the number of slots may generally decrease the amount of deflection in the circumferential direction.

Figure 32:
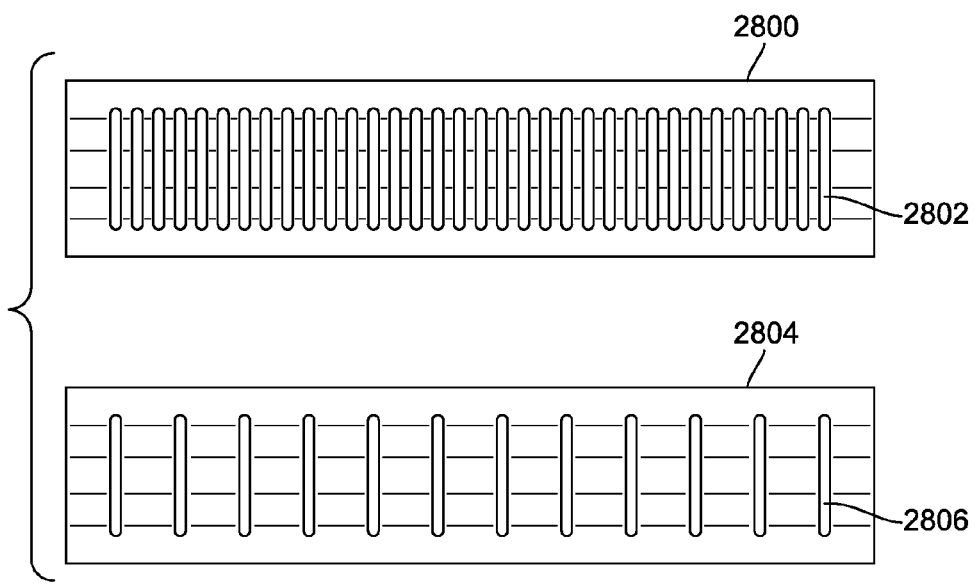
FIG. 32 is a plan view of two preferred embodiments of implant strips with slots with a differing number of slots.

FIG. 32 is a preferred embodiment of first implant strip 2800 and second implant strip 2804. First implant strip 2800 includes first slots 2802 and second implant strip 2804 includes second slots 2806. Preferably, the number of slots comprising first slots 2802 is greater than the number of slots comprising second slots 2806.

Figure 33:
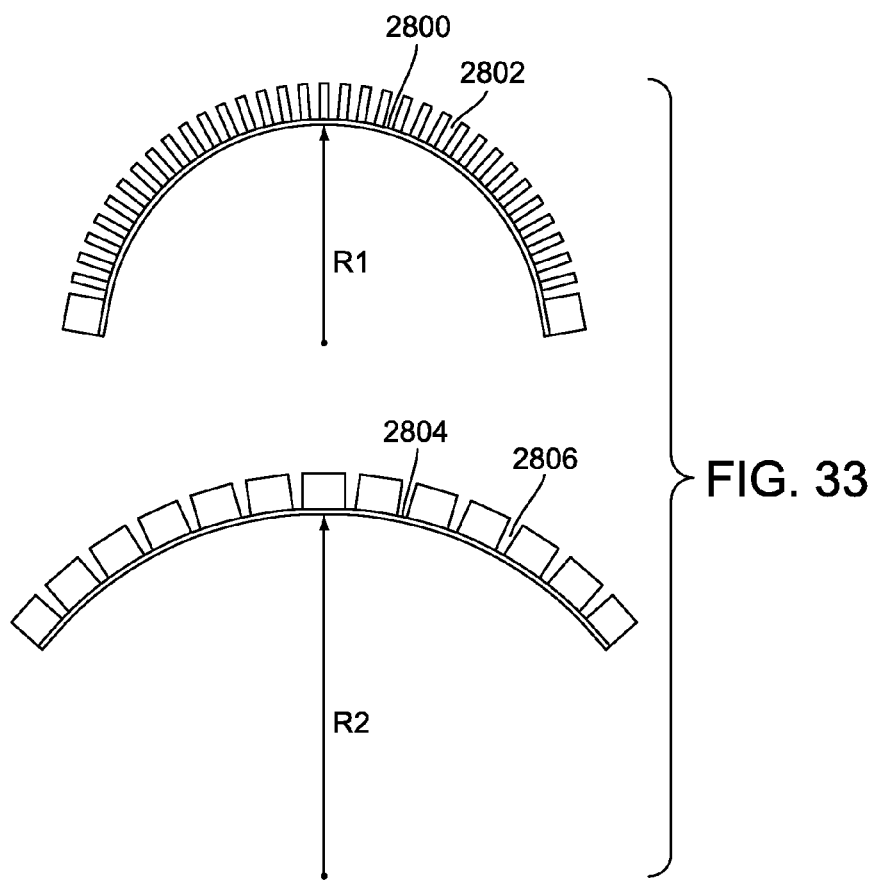
FIG. 33 is a plan view of two preferred embodiments of implant strips with slots undergoing circumferential deflection.

Referring to FIG. 33, first implant strip 2800 and second implant strip 2804 have different deflection characteristics since first implant strip 2800 has a greater number of slots than second implant strip 2804. In this embodiment, first implant strip 2800 can deflect or curve more in the circumferential direction than second implant strip 2804. In particular, first implant strip 2800 has a first radius of curvature R1 than is smaller than a second radius of curvature R2 associated with second implant strip 2804.

By varying the radius of curvature of an implant strip in this manner, the tightness of coiling associated with an implant strip may be varied. Generally, a tighter coil provides more surface area over which to receive axial loads from adjacent vertebrae and thereby increases the strength of the implant strip in the axial direction.

In the previous embodiment, slots of different widths are used to modifying the deflecting properties of an implant strip. In other embodiments, the spacing between slots could vary. In still other embodiments, the orientation of the slots may vary as well. Additionally, in some embodiments, the slots could have different shapes such as oval, round, hexagonal or any type of polygon or irregular shape. These various shapes can be used singularly or in any desired combination.

Figure 34:
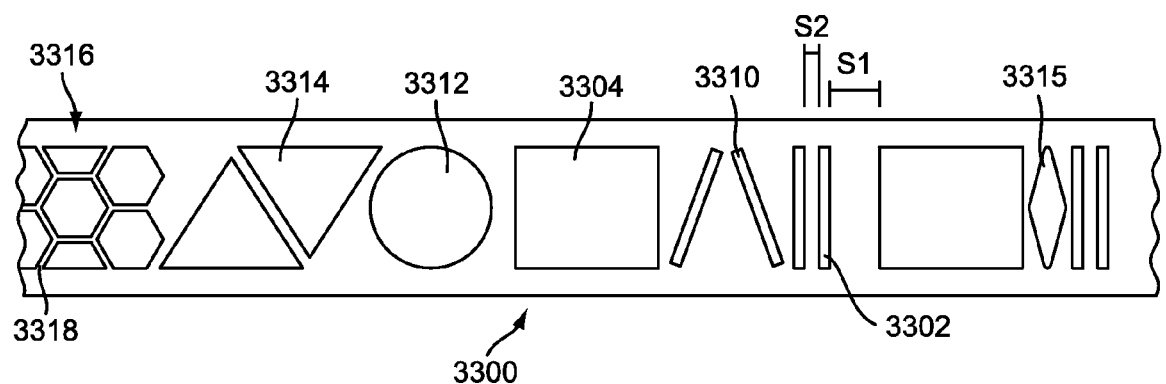
FIG. 34 is a plan view of a preferred embodiment of an implant strip with different slots.

In another embodiment, shown in FIG. 34, a portion of implant strip 3300 includes a variety of punched out shapes configured to change the deflecting characteristics of implant strip 3300. In some embodiments, implant strip 3300 may include thin slots 3302 and wide slots 3304. In this embodiment, the spacing between slots varies from spacing S1 to spacing S2. In this exemplary embodiment, spacing S1 is much larger than spacing S2. In other embodiments, the spacing between slots could be any length, and could vary over implant strip 3300.

In some cases, the orientation of slots could be modified. In some embodiments, implant strip 3300 may include angled slots 3310. Generally, angled slots 3310 may be oriented in any direction, including, in other embodiments, perpendicular to thin slots 3302.

Additional shapes for cutouts are also illustrated in FIG. 34. In some embodiments, implant strip 3300 may include circular cutouts 3312, triangular cutouts 3314 or diamond cutouts 3315. Furthermore, in some cases, the various shapes could be repeating or non-repeating, including various geometric patterns such as honeycomb-like cutouts 3316. In this case, the remaining portions of implant strip 3300 may be configured as lattice 3318.

The various shapes and patterns illustrated in FIG. 34 are only meant to be exemplary. In some embodiments, a single size, shape and spacing for cutouts or slots may be used. In other embodiments, a variety of different shapes for cutouts or slots including regular or irregular spacing between shapes may be used. By using slots or cutouts of varying widths, sizes, orientations and various spacing between slots or cutouts, the deflection properties and the coiling properties of implant strip 3300 may be tuned.

Preferably, implant strips may be configured to permanently deflect in some situations. Generally, vertebrae are not completely symmetric and therefore the spacing between two adjacent vertebrae may vary. Using an implant strip that is configured to partially permanently deflect at some portions allows for a more natural fit of the implant strip.

Figure 35:
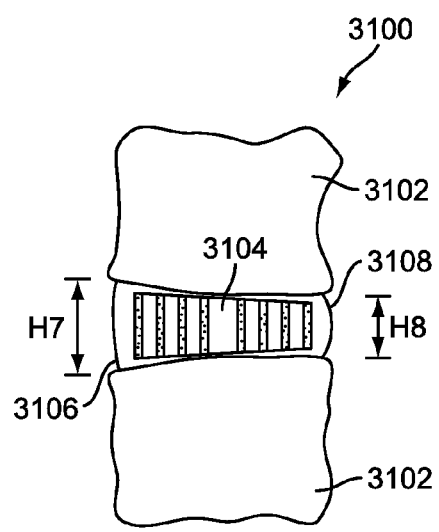
FIG. 35 is a schematic view of a preferred embodiment of an implant strip partially permanently deflecting.

FIG. 35 is a schematic view of a preferred embodiment of a portion of spinal column 3100, including vertebrae 3102. Implant strip 3104 has been inserted between vertebrae 3102 to replace a spinal disc. In this embodiment, the spacing between vertebrae 3102 varies. In particular, at front side 3106 of spinal column 3100, vertebrae 3102 are separated by a height H7 while at rear side 3108 of spinal column 3100, vertebrae 3102 are separated by a height H8 that is less than height H7. Preferably, implant strip 3104 has partially permanently deflected at rear side 3108, allowing for a natural fit. It should be understood that implant strip 3104 has only partially permanently deflected at rear side 3108. Generally, implant strip 3104 is configured to continue axial deflection under increased axial loads at front side 3106 and rear side 3108.

Using the configuration described here, the shape of implant strip 3104 is preferably automatically customized. In some regions between adjacent vertebrae, such as the narrow region discussed above, the implant strip may plastically deform to adjust to natural contours of the adjacent vertebrae. In other regions, such as the wider region discussed above, the implant strip may remain extended or minimally deflected to fully fill in the spaces between vertebrae. In this manner, the implant strip preferably performs a similar function to a spinal disc.

Preferably, an implant strip may include provisions for facilitating coiling of the implant strip during implantation into a spine. In a preferred embodiment, a curved tube may be used to facilitate coiling of an implant strip. The following embodiment is intended to illustrate a provision for facilitating coiling of any type of implant strip. It should be understood that the following procedure may be used to facilitate the implantation of any of the various implant strips discussed earlier as well as other possible implant strips.

Figure 36:
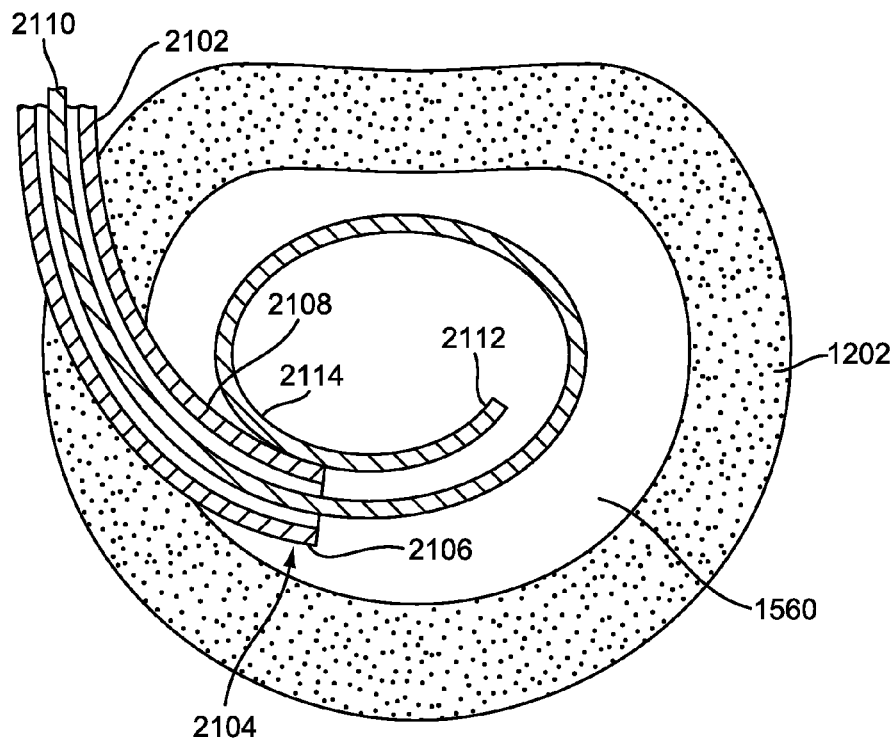
FIG. 36 is a plan view of a preferred embodiment of a delivery device used for facilitating coiling of an implant strip.

FIG. 36 is a preferred embodiment of implant strip 2110 being inserted into cavity 1560 of intervertebral disc 1202. In this embodiment, the insertion of implant strip 2110 is facilitated by delivery device 2102. Delivery device 2102 may be a catheter or similar tube configured for receiving implant strip 2110. Preferably, distal end 2104 of delivery device 2102 is disposed just inside of cavity 1560 and includes curved deforming tip 2106.

As implant strip 2110 is inserted, curved deforming tip 2106 helps facilitate some bending of implant strip 2110 in the circumferential direction. As insertion of implant strip 2110 continues, intermediate portion 2114 of implant strip 2110 is further coiled by inner curved portion 2108 of delivery device 2102. This arrangement further facilitates the coiling of distal end 2112 of implant strip 2110 towards the center of cavity 1560. Using delivery device 2102 allows for increased control of coiling of implant strip 2110 during implantation.

In some embodiments, a spinal implant strip may be used to repair a herniated intervertebral disc. This may be achieved by using similar techniques for removing the herniated portion of the disc. Following this, a spinal implant strip may be inserted into the removed portion of the disc.

Figure 37:
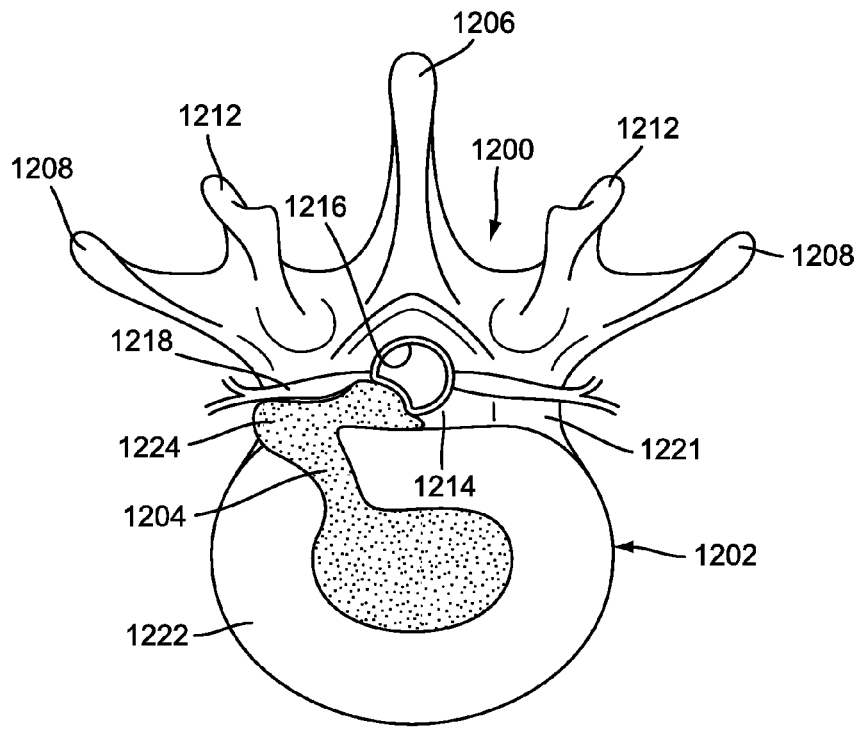
FIG. 37 is a top down view of a preferred embodiment of a herniated intervertebral disc.

FIG. 37 is a plan view similar to that of FIG. 2, illustrating a herniated or traumatized intervertebral disc 1202. As shown, the nucleus pulposus 1224 is protruding from the intervertebral disc 1202 through a cut or flaw 1204 in the intervertebral disc 1202. The protruding nucleus pulposus 1224 impinges on one of the exiting nerves 1218 as well as the spinal cord 1216 or cauda equina.

Figure 38:
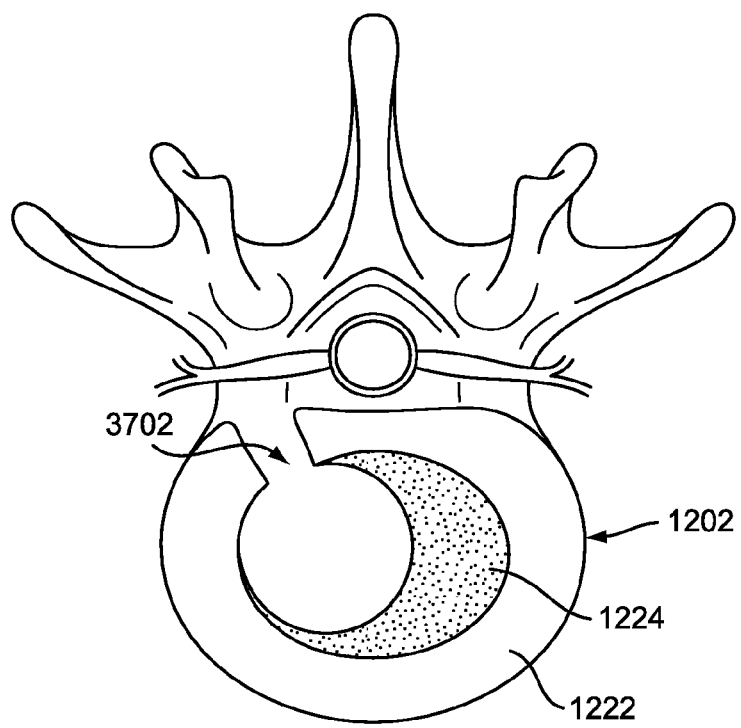
FIG. 38 is a top down view of a preferred embodiment of a herniated disc after partial discectomy.

In cases where an intervertebral disc is herniated, such as is shown here, portions of nucleus pulposus 1224 may be removed, as seen in FIG. 38. This may be achieved using standard surgical techniques or techniques similar to those discussed in the previous embodiments illustrated in FIGS. 6-8. In some cases, a partial discectomy may be also performed through a single tube or double tube. At this point, recess 3702 is left open within disc annulus 1222.

Figure 39:
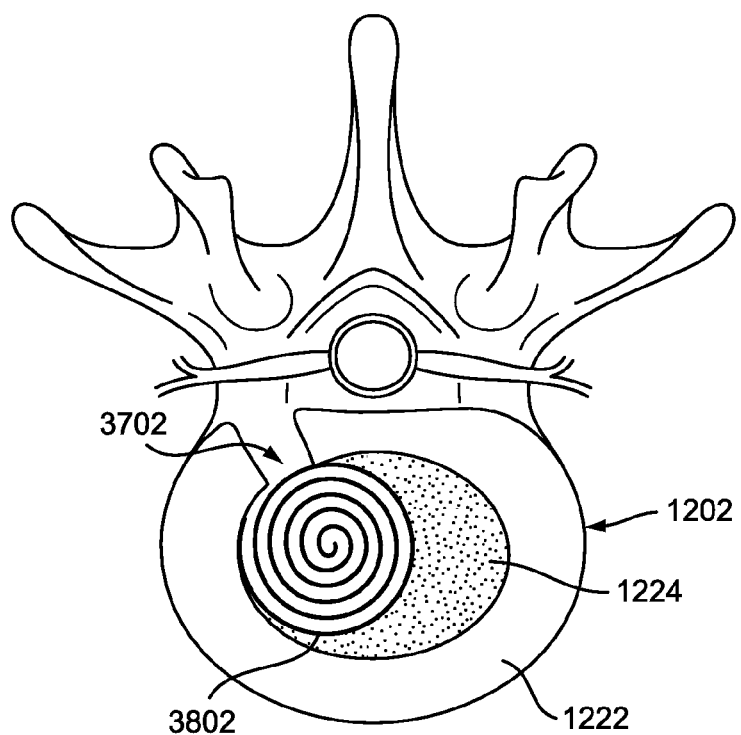
FIG. 39 is a top down view of a preferred embodiment of a herniated disc with an implant strip inserted.

Preferably, implant strip 3802 may be inserted into recess 3702 to repair intervertebral disc 1202, as seen in FIG. 39. This may be accomplished using similar techniques to those previously discussed for implanting a spinal strip illustrated in FIGS. 6-8. As noted in the embodiment shown in FIGS. 6-8, implant strip 3802 may be inserted using a single tube or double tube technique. Using this preferred arrangement, implant strip 3802 may be configured to replicate the mechanical properties of nucleus 1224.

Using the various arrangements for a spinal implant strip discussed in this detailed description provides for improved utility over prior designs. Each of these designs is versatile since various types of implant strips may be used for replacing various kinds of spinal discs. Also, each of these arrangements provides for a single piece device that does not experience the wear or generate particulate debris that may be associated with multi-piece designs. Finally, using the materials and designs discussed in this detailed description, the implant strips are preferably configured to either remain rigid or maintain a general spring-like state, without undergoing any fatigue or mechanical failure.

Embodiments of the present invention can provide for continuity of the spine. The term "continuity of the spine" generally refers to the concept providing an actual mechanical bridge between two distinct vertebral bodies. In some embodiments, this implant device provides for a mechanical bridge while also allowing motion between the two distinct vertebral bodies. This arrangement can approximate the natural biomechanics of the spine.

By applying principles or features of the present invention, a surgeon can implant a device to restore the original anatomical height of the disk, thereby restoring normal forces across the spine. The surgeon can also select an implant device that can provide decompression of the nerves in the spinal foramen and canals. This implant device can provide a post-implantation height greater than or less than the original anatomical height of the disk. This implant device can also provide a post-implantation configuration that optimizes the relative position between two vertebrae. In some cases, this post-implantation configuration can be used to correct scoliosis or spondylolisthesis.

While various embodiments of the invention have been described, the description is intended to be exemplary, rather than limiting and it will be apparent to those of ordinary skill in the art that many more embodiments and implementations are possible that are within the scope of the invention. Accordingly, the invention is not to be restricted except in light of the attached claims and their equivalents. Also, various modifications and changes may be made within the scope of the attached claims.

We claim:

1. A spinal prosthesis, comprising:
    an elongated implant strip extending in a longitudinal direction when in an uncoiled configuration and having a first lateral edge and a second lateral edge opposite to the first lateral edge, wherein the implant strip is configured to be coiled within itself substantially within a horizontal plane and is configured for insertion between two adjacent vertebrae with the first lateral edge configured to face a first vertebra of the two adjacent vertebrae and the second lateral edge configured to face a second vertebra of the two adjacent vertebrae, and wherein the first lateral edge and the second lateral edge are treated to promote bone growth;
    the implant strip comprising a first portion having a first rigidity and a second portion having a second rigidity;
    wherein the first portion and the second portion are made of the same material;
    wherein the second rigidity is less than the first rigidity;
    wherein the first portion extends in the longitudinal direction in a first horizontal plane, wherein the second portion extends in the longitudinal direction in a second horizontal plane, and wherein the first horizontal plane is different from the second horizontal plane;
    wherein the second portion is configured to deflect under an axial load before the first portion deflects;
    wherein, when viewed in a cross-section taken perpendicularly to the longitudinal direction, the first portion comprises an elongated upper vertical side extending in a vertical direction and having the first lateral edge and an elongated lower vertical side extending in the vertical direction and having the second lateral edge; and
    wherein the second portion comprises a protruding portion joined to the upper vertical side and the lower vertical side and extending away from the upper vertical side and the lower vertical side.

2. The spinal prosthesis according to claim 1, wherein the second portion contains a structural feature that provides increased deflection in comparison to the first portion.

3. The spinal prosthesis according to claim 1, wherein the first lateral edge and the second lateral edge are treated to promote bone growth by use of a coating of bone growth promoting agent.

4. The spinal prosthesis according to claim 1, wherein the second portion is configured to partially permanently deflect.

5. The spinal prosthesis according to claim 1, wherein the spinal prosthesis is configured to provide for continuity of a spine by being configured to provide a mechanical bridge between the two adjacent vertebrae.

6. The spinal prosthesis according to claim 1, wherein the second portion is configured to provide a restoring force following a twisting of the implant strip under a rotational force.

7. The spinal prosthesis according to claim 1, wherein the second portion is configured to provide a restoring force following lateral deflection of the implant strip under a lateral force.

8. The spinal prosthesis according to claim 1, wherein the second portion is configured to provide a restoring force following bending of the implant strip under bending forces.

9. The spinal prosthesis according to claim 1, wherein the second portion is configured to provide a restoring force following axial deflection of the implant strip under axial forces.

10. The spinal prosthesis according to claim 1, wherein the spinal prosthesis is generally configured to experience less stress than an expected stress; wherein the expected stress is less than an endurance limit.

11. The spinal prosthesis according to claim 1, wherein the spinal prosthesis is configured to provide for continuity of a spine by being configured to provide a mechanical bridge between the first vertebra and the second vertebra.

12. The spinal prosthesis according to claim 1, wherein the material of the first portion and the second portion is metal.

13. The spinal prosthesis according to claim 1, wherein, when in an undeflected configuration, the upper vertical side and the lower vertical side are disposed along a vertical longitudinal axis and wherein the protruding portion of the second portion protrudes away from the vertical longitudinal axis.

14. A spinal prosthesis, comprising:
an elongated implant strip extending in a longitudinal direction when in an uncoiled configuration and having a first lateral edge and a second lateral edge opposite to the first lateral edge, wherein the implant strip is configured to be coiled within itself substantially within a horizontal plane and is configured for insertion between two adjacent vertebrae with the first lateral edge configured to face a first vertebra of the two adjacent vertebrae and the second lateral edge configured to face a second vertebra of the two adjacent vertebrae, and wherein the first lateral edge and the second lateral edge are treated to promote bone growth;
the implant strip comprising a first portion having a first rigidity and a second portion having a second rigidity;
wherein the first portion and the second portion are made of the same material;
wherein the second rigidity is less than the first rigidity;
wherein the first portion extends in the longitudinal direction in a first horizontal plane, wherein the second portion extends in the longitudinal direction in a second horizontal plane, and wherein the first horizontal plane is different from the second horizontal plane;
wherein the second portion is configured to deflect under an axial load before the first portion deflects;
wherein, when viewed in a cross-section taken perpendicularly to the longitudinal direction, the first portion comprises an upper vertical side having the first lateral edge and a lower vertical side having the second lateral edge;
wherein the second portion comprises a protruding portion joined to the upper vertical side and the lower vertical side and extending away from the upper vertical side and the lower vertical side;
wherein, when viewed in a cross-section taken perpendicularly to the longitudinal direction, the second portion comprises a first sloped portion joined to and extending away from the upper vertical side at a first angle, a second sloped portion joined to and extending away from the lower vertical side at a second angle, and an intermediate portion extending vertically between the first sloped portion and the second sloped portion from an end of the first sloped portion opposite to the upper vertical side to an end of the second sloped portion opposite to the lower vertical side; and
wherein the first angle and the second angle vary when the second portion deflects under the axial load.

15. The spinal prosthesis according to claim 14, wherein the first sloped portion and the second sloped portion are curved when viewed in a cross-section taken perpendicularly to the longitudinal direction.

16. A spinal prosthesis, comprising:
an elongated implant strip extending in a longitudinal direction when in an uncoiled configuration and having a first lateral edge and a second lateral edge opposite to the first lateral edge, wherein the implant strip is configured to be coiled within itself substantially within a horizontal plane and is configured for insertion between two adjacent vertebrae with the first lateral edge configured to face a first vertebra of the two adjacent vertebrae and the second lateral edge configured to face a second vertebra of the two adjacent vertebrae, and wherein the first lateral edge and the second lateral edge are treated to promote bone growth;
the implant strip comprising a first portion having a first rigidity and a second portion having a second rigidity;
wherein the first portion and the second portion are made of the same material;
wherein the second rigidity is less than the first rigidity;
wherein the first portion extends in the longitudinal direction in a first horizontal plane, wherein the second portion extends in the longitudinal direction in a second horizontal plane, and wherein the first horizontal plane is different from the second horizontal plane;
wherein the second portion is configured to deflect under an axial load before the first portion deflects;
wherein, when viewed in a cross-section taken perpendicularly to the longitudinal direction, the first portion comprises an upper vertical side having the first lateral edge and a lower vertical side having the second lateral edge;
wherein the second portion comprises a protruding portion joined to the upper vertical side and the lower vertical side and extending away from the upper vertical side and the lower vertical side; and
wherein the implant strip defines a plurality of slots, each slot extending from the upper vertical side through the protruding portion and into the lower vertical side.

17. A spinal prosthesis, comprising:
an implant strip extending in a longitudinal direction when in an uncoiled configuration and having a first lateral edge and a second lateral edge opposite to the first lateral edge, wherein the implant strip is configured for insertion between two adjacent vertebrae, including a first vertebra and a second vertebra, and wherein the first lateral edge and the second lateral edge are treated to promote bone growth;
a first portion of the implant strip comprising a first lateral side portion and a second lateral side portion;
a second portion having a rigidity less than a rigidity of the first portion of the implant strip;
wherein the first lateral side portion, the second portion, and the second lateral side portion extend in the longitudinal direction, and the second portion is disposed between the first lateral side portion and the second lateral side portion;
wherein the first portion and the second portion are made of the same material;
wherein the second portion is configured to deflect under an axial load before the first portion deflects;
wherein the implant strip is configured to be coiled within itself substantially within a horizontal plane such that the first lateral side portion is configured to be disposed adjacent to the first vertebra and the second lateral side portion is configured to be disposed adjacent to the second vertebra;
wherein, when viewed in a cross-section taken perpendicularly to the longitudinal direction, the first lateral side portion comprises an elongated upper vertical side extending in a vertical direction and having the first lateral edge and the second lateral side portion comprises an elongated lower vertical side extending in the vertical direction and having the second lateral edge; and
wherein the second portion comprises a protruding portion joined to the upper vertical side and the lower vertical side and extending away from the upper vertical side and the lower vertical side.

18. The spinal prosthesis according to claim 17, wherein the implant strip is configured to coil during insertion between two adjacent vertebrae, and wherein the first lateral edge and the second lateral edge are treated to promote bone growth by use of a coating of bone growth promoting agent.

19. The spinal prosthesis according to claim 17, wherein the second portion has structural properties different from the first portion, which cause the second portion to deflect before the first portion.

20. The spinal prosthesis according to claim 17, wherein the spinal prosthesis is configured to provide for continuity of a spine by being configured to provide a mechanical bridge between the first vertebra and the second vertebra.

* * * * *